(12) United States Patent
Li et al.

(10) Patent No.: US 6,184,018 B1
(45) Date of Patent: Feb. 6, 2001

(54) β-GLUCOSIDASE CODING SEQUENCES AND PROTEIN FROM ORPINOMYCES PC-2

(75) Inventors: Xin-Liang Li; Lars G. Ljungdahl, both of Athens; Huizhong Chen, Lawrenceville; Eduardo A. Ximenes, Athens, all of GA (US)

(73) Assignee: University of Georgia Research Foundation, Inc., Athens, GA (US)

( * ) Notice: Under 35 U.S.C. 154(b), the term of this patent shall be extended for 0 days.

(21) Appl. No.: 09/306,593

(22) Filed: May 6, 1999

Related U.S. Application Data

(60) Provisional application No. 60/084,494, filed on May 6, 1998.

(51) Int. Cl.$^7$ .............................. C12N 9/38; C07H 21/04
(52) U.S. Cl. ..................... 435/209; 435/183; 435/252.3; 435/320.1; 435/69.1; 435/254.21; 435/254.33; 435/254.5; 435/254.6; 435/254.11; 435/252.35; 435/252.31; 435/255.5; 435/254.23; 536/23.1; 536/23.2
(58) Field of Search ................................ 435/209, 252.3, 435/320.1, 69.1, 183, 254.21, 252.33, 254.5, 254.6, 254.4, 252.35, 252.31, 255.5, 254.23

(56) References Cited

PUBLICATIONS

Ximenes et al. (1998) "Cloning and Sequencing of a β–Glucosidase Gene from the Anaerobic Fungus Orpinomyces sp. Strain PC–2 and Its Expression in *Saccharomyces cerevisiae*" Abstract. General Meeting of the American Society of Microbiology. 98:337.

Archer and Peberdy (1997) "The Molecular Biology of Secreted Enzyme Production by Fungi" *Critical Reviews in Biotechnology* 17:273–306.

Bhat et al. (1993) "Purification and Characterization of an Extracellular β–Glucosidase from the Thermophilic Fungus *Sporotrichum thermophile* and Its Influence on Cellulase Activity" *Journal of General Microbiology* 139:2825–2832.

Borneman et al. (1989) "Fermentation Products and Plant Cell Wall–degrading Enzymes Produced by Monocentric and Polycentric Anaerobic Ruminal Fungi" *Applied and Environmental Microbiology* 55:1066–1073.

Breves et al. (1997) "Genes Encoding Two Different β–Glucosidases of *Thermoanaerobacter brockii* Are Clustered in a Common Operon" *Applied and Environmental Microbiology* 63:3902–3910.

Chen et al. (1998) "Two Genes of Anaerobic Fungus Orpinomyces sp. Strain PC–2 Encoding Cellulases with Endoglucanase Activities May Have Arisen by Gene Duplication" *FEMS Microbiology Letters* 159:63–68.

Chen et al. (1997) "Sequencing of a 1,3–1,4–β–D–Glucanase (Lichenase) from the Anaerobic Fungus Orpinomyces Strain PC–2: Properties of the Enzyme Expressed in *Escherichia coli* and Evidence that the Gene Has a Bacterial Origin" *Journal of Bacteriology* 179:6028–6034.

Chen et al. (1995) "A Cyclophilin from the Polycentric Anaerobic Rumen Fungus Orpinomyces sp. Strain PC–2 Is Highly Homologous to Vertebrate Cyclophilin B" *Proc. Natl. Acad. Sci. USA* 92:2587–2591.

Chen et al. (1994) "Isolation and Properties of an Extracellular β–Glucosidase from the Polycentric Rumen Fungus Orpinomyces sp. Strain PC–2" *Applied and Environmental Microbiology* 60:64–70.

Chen et al. (1992) "Purification and Characterization of Two Extracellular β–Glucosidases from *Trichoderma reesei*" *Biochimica et Biophysica Acta* 1121:54–60.

Cummings and Fowler (1996) "Secretion of *Trichoderma reesei* β–Glucosidase by *Saccharomyces cerevisiae*" *Curr. Genet.* 29:227–233.

Desrochers et al. (1981) "High Production of β–Glucosidase in *Schizophyllum commune:* Isolation of the Enzyme and Effect of the Culture Filtrate on Cellulose Hydrolysis" *Applied and Environmental Microbiology* 41:222–228.

Fanutti et al. (1995) "The Conserved Noncatalytic 40–Residue Sequence in Cellulases and Hemicellulases from Anaerobic Fungi Functions as a Protein Docking Domain" *Journal of Biological Chemistry* 270:29314–29322.

Freer, S.N. (1993) "Kinetic Characterization of a β–Glucosidase from a Yeast, *Candida wickerhamii*" *The Journal of Biological Chemistry* 268:9337–9342.

Gräbnitz et al. (1991) "Structure of the β–Glucosidase Gene bglA of *Clostridium thermocellum*" *Eur. J. Biochem.* 200:301–309.

Hays et al. (1996) "Primary Structure of the Cytosolic β–Glucosidase of Guinea Pig Liver" *Biochem. J.* 319:829–837.

Henrissat and Bairoch (1993) "New Families In the Classification of Glycosyl Hydrolases Based On Amino Acid Sequence Similarities" *Biochem. J.* 293:781–788.

Hebraud and Fevre (1990) "Purification and Characterization of an Aspecific Glycoside Hydrolase from the Anaerobic Ruminal Fungus *Neocallimastix frontalis*" *Applied and Environmental Microbiology* 56:3164–3169.

Hoh et al. (1992) "Properties of β–Glucosidase Purified from *Aspergillus niger* Mutants USDB 0827 and USDB 0828" *Appl. Microbiol. Biotechnol.* 137:590–593.

Inoue et al. (1996) "Molecular Cloning and Bacterial Expression of a cDNA Encoding Furostanol Glycoside 26–O–β–Glucosidase of *Costus speciosus*" *FEBS Letters* 389:273–277.

(List continued on next page.)

*Primary Examiner*—Rebecca E. Prouty
*Assistant Examiner*—Richard Hutson
(74) *Attorney, Agent, or Firm*—Greenlee, Winner and Sullivan, P.C.

(57) ABSTRACT

Provided is a novel β-glucosidase from Orpinomyces sp. PC2, nucleotide sequences encoding the mature protein and the precursor protein, and methods for recombinant production of this β-glucosidase.

13 Claims, 5 Drawing Sheets

OTHER PUBLICATIONS

Katayeva et al. (1992) "*Clostridium thermocellum* β–Glucosidases A and B: Purification, Properties, Localization, and Regulation of Biosynthesis" *Enzyme Microb. Technol.* 14:407–412.

Kwon et al. (1992) "Purification and Characterization of Two Extracellular β–Glucosidases from *Aspergillus nidulans*" *FEMS Microbiology Letters* 97:149–154.

Li and Calza (1991) "Kinetic Study of a Cellobiase Purified from *Neocallimastix frontalis* EB188" *Biochimica et Biophysica Acta* 1080:148–154.

Li and Calza (1991) "Purification and Characterization of an Extracellular β–Glucosidase from the Rumen Fungus *Neocallimastix frontalis* EB188" *Enzyme Microb. Technol.* 13:622–628.

Li et al. (1997) "Monocentric and Polycentric Anaerobic Fungi Produce Structurally Related Cellulases and Xylanases" *Applied and Environmental Microbiology* 63:628–635.

Li et al. (1997) "Two Cellulases, CelA and CelC, from the Polycentric Anaerobic Fungus Orpinomyces Strain PC–2 Contain N–Terminal Docking Domains for a Cellulase–Hemicellulase Complex" *Applied and Environmental Microbiology* 63:4721–4728.

Li et al. (1997) "High Molecular Weight Cellulase/Hemicellulase Complexes of Anaerobic Fungi" Abstract O–31. $97^{th}$ General Meeting of the American Society for Microbiology. p. 424.

Liebl et al. (1994) "Comparative Amino Acid Sequence Analysis of *Thermotoga maritima* β–Glucosidase (BglA) Deduced from the Nucleotide Sequence of the Gene Indicates Distant Relationship Between β–Glucosidases of the BGA Family and Other Families of β–1,4–Glycosyl Hydrolases" *Mol. Gen. Genet.* 242:111–115.

Ohmiya et al. (1985) "Isolation and Properties of β–Glucosidase from *Ruminococcus albus*" *Journal of Bacteriology* 161:432–434.

Olsen and Thomsen (1991) "Improvement of Bacterial β–Glucanase Thermostability by Glycosylation" *Journal of General Microbiology* 137:579–585.

Oxtoby et al. (1991) "Nucleotide and Derived Amino Acid Sequence of the Cyanogenic β–Glucosidase (Linamarase) from White Clover (*Trifolium repens* L.)" *Plant Molecular Biology* 17:209–219.

Paavilainen et al. (1993) "Purification, Characterization, Gene Cloning, and Sequencing of a New β–Glucosidase from *Bacillus circulans* subsp. *alkalophilus*" *Applied and Environmental Microbiology* 59:927–932.

Pemberton et al. (1980) "The Role of β–Glucosidase in the Bioconversion of Cellulose to Ethanol" *The Canadian Journal of Chemical Engineering* 58:723–734.

Penttilä et al. (1988) "Efficient Secretion of Two Fungal Cellobiohydrolases by *Saccharomyces cerevisiae*" *Gene* 63:103–112.

Penttilä et al. (1987) "Expression of Two *Trichoderma reesei* Endoglucanases in the Yeast *Saccharomyces cerevisiae*" *Yeast* 3:175–185.

Romanos et al. (1992) "Foreign Gene Expression in Yeast: A Review" *Yeast* 8:423–488.

Rutenburg et al. (1960) "The Histochemical Demonstration of α–D–Glucosidase in Mammalian Tissues" *J. Histochem. Cytochem.* 8:268–272.

Ruttersmith and Daniel (1993) "Thermostable β–Glucosidase and β–Xylosidase from Thermotoga sp. Strain FjSS3–B.1" *Biochemica et Biophysica Acta* 1156:167–172.

Saha et al. (1995) In: *Enzymatic Degradation of Insoluble Carbohydrates*, Eds. Saddler and Penner, M.H. ACS Symposium Series 618, pp. 197–207.

Sanz–Aparicio et al. (1998) "Crystal Structure of β–Glucosidase A from *Bacillus polymyxa*: Insights Into the Catalytic Activity in Family 1 Glycosyl Hydrolases" *J. Mol. Biol.* 275:491–502.

Sternberg et al. (1977) "β–Glucosidase: Microbial Production and Effect on Enzymatic Hydrolysis of Cellulose" *Can. J. Microbiol.* 23:139–147.

Teunissen et al. (1992) "Purification and Characterization of an Extracellular β–Glucosidase from the Anaerobic Fungus Piromyces sp. Strain E2" *Arch. Microbiol.* 158:276–281.

Van Rensburg et al. (1998) "Engineering Yeast for Efficient Cellulose Degradation" *Yeast* 14:67–76.

β-GLUCOSIDASE CODING SEQUENCES AND PROTEIN FROM ORPINOMYCES PC-2

CROSS REFERENCE TO RELATED APPLICATIONS

This application claims priority from United States Provisional Application No. 60/084,494, filed May 6, 1998.

ACKNOWLEDGEMENT OF FEDERAL RESEARCH SUPPORT

This invention was made, at least in part, with funding from the United States Department of Energy (Grant No. DE-FG02 93ER 20127). Accordingly, the United States Government has certain rights in this invention.

BACKGROUND OF THE INVENTION

The field of the present invention is the area of cellulolytic enzymes, nucleotide sequences encoding them and recombinant host cells and methods for producing them.

Cellulosic biomass, photosynthesized by solar energy with $CO_2$ and $H_2O$, is one of the most important renewable energy resources on earth. Its effective utilization through biological processes is one approach to overcoming the shortage of foods, feeds and fuels, expected as a consequence of the explosive increase in human population [Ohmiya et al. (1997) Biotechnol. Gen. Engineer. Rev. 14:365–414]. Several types of enzymes are required for complete hydrolysis of cellulose to glucose, including endoglucanase, exoglucanase or cellobiohydrolase and β-glucosidase [Filho (1996) Can. J. Microbiol. 42:1–5].

β-Glucosidase (β-D-glucoside glucohydrolase; EC 3.2.1.21) is common among plants, fungi and bacteria. β-Glucosidase has aroused considerable interest primarily because of its involvement in the biological conversion of cellulosic material. The enzymatic saccharification of cellulosic materials to D-glucose is known to require the synergistic action of three classes of enzymes: endo-1,4-β-D-glucanohydrolase (EC 3.2.1.74), 1,4-β-D-cellobiohydrolase (EC 3.22.1.91), and 1,4-β-D-glucosidase (β-glucosidase; EC 3.2.1.21). Endo-1,4-β-D-glucanases act randomly on cellulose chains, whereas 1,4-β-D-cellobiohydrolases cleave cellobiosyl residues from the ends of cellulose chains, generating cellobiose as the main product. β-Glucosidase acts to liberate D-glucose units from cellobiose, cello-oligosaccharides, and other glucosides [Freer (1993) J. Biol. Chem. 268:9337–9342].

Anaerobic fungi have been isolated from the alimentary tracts of herbivores and other environments [Li et al. (1997) Appl. Environ. Microbiol. 63:628–635; Wubah and Kim (1994) Abstracts of the 94th Gen. Meet. of the American Society for Microbiology. Las Vegas, Nev., USA]. They produce highly active hydrolytic enzymes [Borneman et al. (1989) Appl. Environ. Microbiol. 55:1066–1073]. Genes encoding several cellulases and xylanases have been cloned and sequenced from anaerobic fungi Neocallimastix patriciarum [Black et al. (1994) Biochem. J. 299:381–387; Denman et al. (1996) Appl. Environ. Microbiol. 62:1889–1896; Gilbert et al. (1992) Mol. Microbiol. 6:2065–2072; Zhou et al. (1994) Biochem. J. 297:359–364], Piromyces sp. [Fanuti et al. (1995) J. Biol. Chem. 270:29314–29322] and Orpinomyces sp. [Chen et al. (1998) FEMS Microbiol. Letts. 159:63–68; Li et al. (1997) Appl. Environ. Microbiol. 63:628–635]. In addition, genes coding for three mannanases from Piromyces sp. [Fanutti et al. (1995) J. Biol. Chem. 270:29314–29322; Millward-Sadler et al. (1996) FEMS Microbiol. Lett. 141:183–188] and one 1,3-1,4-β-D-glucanase from Orpinomyces sp. [Chen et al. (1997) J. Bacteriol. 179:6028–6034] have been cloned and sequenced. However, genes coding for β-glucosidases of anaerobic fungi have not been reported even though several such enzymes from Neocallimastix [Herbaud and Fevre (1990) Appl. Environ. Microbiol. 56:3164–3169; Li and Calza (1991 A) Enzyme Microb. Technol. 13:622–628; Li and Calza (1991B) Biochem. Biophys. Acta 1080:148–154], Orpinomyces [Chen et al. (1994) Appl. Environ. Microbiol. 60:64–70], and Piromyces [Teunissen et al. (1992) Arch. Microbiol. 158:276–281] have been purified and characterized.

There is a longfelt need in the art for β-glucosidase enzymes with catalytic properties which allow for improved saccharification of cellulosic materials and partial breakdown products thereof

SUMMARY OF THE INVENTION

It is an object of the present invention to provide a β-glucosidase and the nucleotide sequences encoding it from Orpinomyces PC-2. The coding sequence for the protein, including its signal peptide and the stop codon, is given in SEQ ID NO:1, nucleotides 39–2012. The mature β-glucosidase is encoded at nucleotides 87–2009, exclusive of the stop codon. The deduced amino acid sequences of the signal peptide and of the mature protein is given in SEQ ID NO:2. Alternative β-glucosidase sequences are SEQ ID NO:2, amino acids 24–641 or SEQ ID NO:2, amino acids 33–641.

Also within the scope of the present invention are non-naturally occurring recombinant DNA molecules comprising all synonymous sequences encoding the β-glucosidase of the present invention, recombinant host cells comprising the aforementioned DNA molecules, and methods for the synthesis of recombinant β-glucosidase of the present invention. Preferably, the coding sequence for the β-glucosidase is operably linked to transcription and translation control sequences functional in the desired host cell. A desired recombinant host cell is a yeast, as specifically exemplified, a Saccharomyces cerevisiae cell genetically engineered to contain and express the β-glucosidase coding sequences of the present invention. Other recombinant host cells of the present invention include, without limitation, fungi such as Aspergillus spp., Trichoderma spp., Pichia spp., Aureobasidium spp. and bacteria, including but not limited to Bacillus spp.

BRIEF DESCRIPTION OF THE DRAWINGS

FIG. 2A shows the results of SDS-PAGE stained with Coomassie brilliant blue R-250; FIG. 2B is a photograph of a β-glucosidase zymogram gel. Lane S, protein molecular mass standards; lane 1, crude culture supernatant (10 µg); lane 2, purified secreted BglA (2 µg); lane 3, crude cell extract (60 µg); lane 4, partially purified Bgl1 (2 µg); lane 5, partially purified Bgl2 (2 µg); lane 6, purified secreted BglA (2 µg); lane 7, Bgl1 (2 µg); lane 8, Bgl2 (2 µg).

FIG. 4A shows the effect of pH on the activity determined at 40° C.; and FIG. 4B shows the effect of temperatures on the activity determined at pH 6.0. Symbols: (●), pNPGase activity; (■), cellobiase activity.

DETAILED DESCRIPTION OF THE INVENTION

Figure 1:
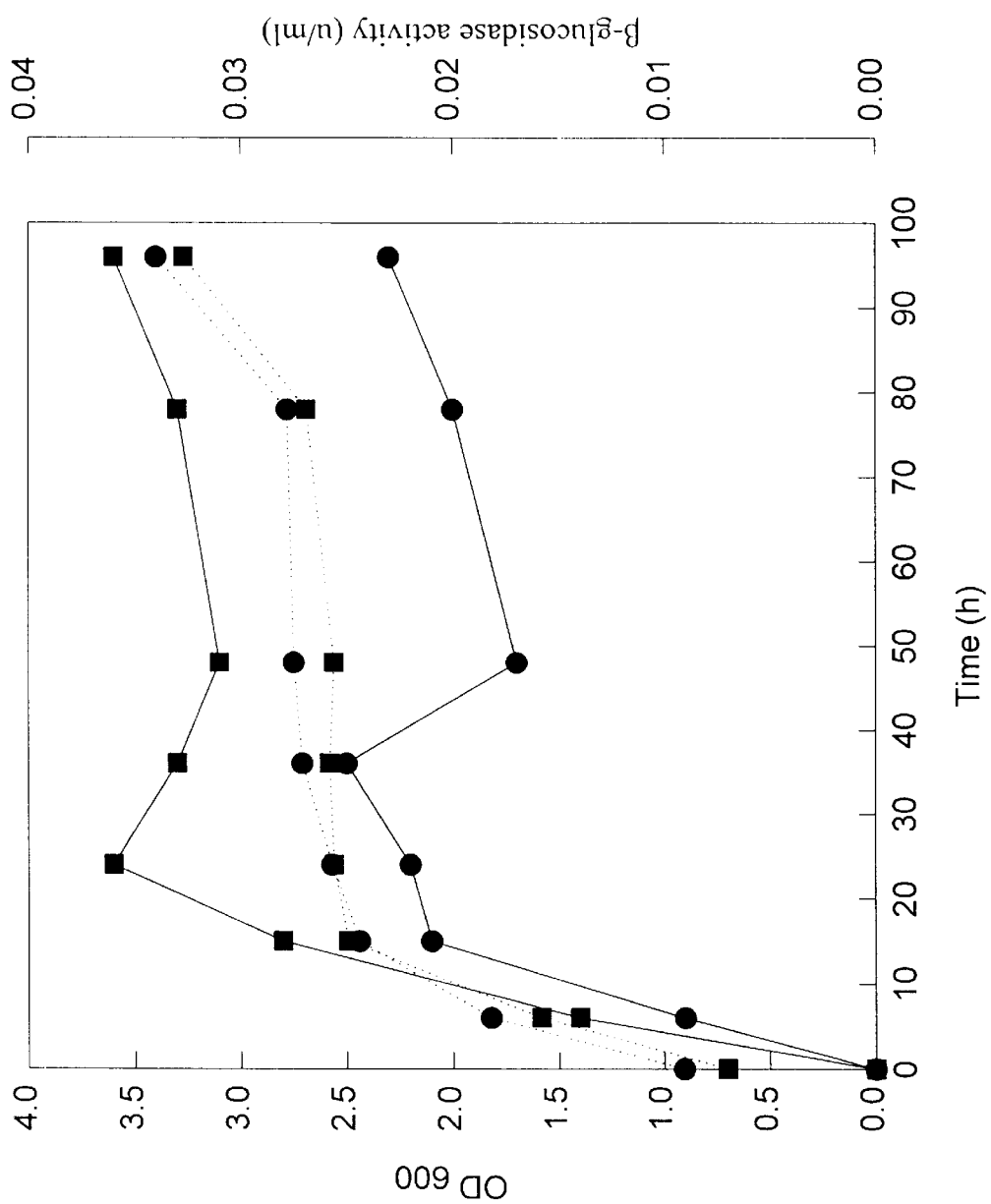
FIG. 1 illustrates β-glucosidase production by recombinant S. cerevisiae cultures after galactose induction. An aliquot of an overnight culture grown in DOB medium was used to inoculate raffinose-YPD medium. After growth to an $OD_{600}$ of 1.0, sterile galactose was added. Samples were withdrawn at times points shown in the figure. $OD_{600}$ of control culture (■-■), $OD_{600}$ (●--●) and β-glucosidase activity of cell extract (■-■) and culture medium (●--●) of transformant #7 were determined. Culture conditions, preparation of the samples, and enzyme assay were described in the Examples. The control culture corresponds to the yeast containing the pYES2 without any insert.

Abbreviations used in the present specification include the following: aa, amino acid(s); bp, base pair(s); CD, catalytic domain(s); cDNA, DNA complementary to RNA; GCG, Genetics Computer Group, Madison, Wis.; CMC, carboxymethyl cellulose; CMCase, carboxymethyl cellulase; FPase, filter paper-ase; HMWC, high-molecular weight complex(es); IPTG, isopropyl-β-D-thiogalactoside; OSX, oat spelt xylan; ORF, open reading frame; RBB, remazol brilliant blue; RP, repeated peptide(s); pfu, plaque forming units.

Orpinomyces sp. strain PC-2, a polycentric anaerobic fungus isolated from the rumen of a cow, produces high levels of β-glucosidase as well as endoglucanase, cellobiohydrolase and xylanase [Borneman et al. (1989) *Appl. Environ. Microbiol.* 55:1066–1073]. A β-glucosidase secreted into the culture supernatant has been recently purified and characterized [Chen et al. (1994) *Appl. Environ. Microbiol.* 60:64–70]. Different hydrolytic enzymes of Orpinomyces have been found to function individually or in high molecular weight enzyme complexes (HMWC) [Chen et al. (1997) *J. Bacteriol.* 179:6028–6034; Chen et al. (1998) *FEMS Microbiol. Letts.* 159:63–68; Li et al. (1997) *Appl. Environ. Microbiol.* 63:628–635; Li et al. (1997) *Appl. Environ. Microbiol.* 63:4721–4728]. The enzyme complexes purified from residual solid substrate of the fungal culture have been shown to contain β-glucosidase activity [Li et al. (1997) Abstract O-31, p. 424. 97$^{th}$ Gen. Meet. Am. Soc. Microbiol. American Society for Microbiology, Washington D.C., Romanos, M. A., C. A. Scorer, and J. J. Clare. 1992. *Yeast* 8:423–488], indicating that β-glucosidase(s) serve as components of the HMWCs produced by the fungus.

Many hydrolytic enzymes sequenced to date contain, in addition to catalytic domains, a non-catalytic repeated peptide domain (NCRPD), which functions as a dockerin in the cellulosome of *Clostridium thermocellum* [Béguin and Lemaire (1996) *Critical Rev. Biochem. Mol. Biol.* 31:201–236] and cellulosome-like complexes of anaerobic fungi [Fanutti et al. (1995) *J. Biol. Chem.* 270:29314–29322]. Polyclonal antibodies raised specially against the NCRPD of Orpinomyces XynA cross-reacted with a number of polypeptides in the culture media of Orpinomyces and Neocallimastix grown on cellulose [Li et al. (1997) *Appl. Environ. Microbiol.* 63:628–635; Li et al. (1997) *Appl. Environ. Microbiol.* 63:4721–4728], suggesting that a number of NCRPD-containing enzymes remain to be isolated. To isolate cDNAs coding for NCRPD-containing polypeptides, we used the XynA NCRPD specific antibodies to screen an Orpinomyces cDNA library [Chen et al. (1995) *Proc. Natl. Acad. Sci. USA* 92:2587–2591]. Twenty-five positive plaques were isolated after screening $1.0 \times 10^5$ plaque forming units. Sequencing of the inserted cDNAs in the pBluescripts after being excised from pure positive lambda plaques revealed that several presented different lengths of cDNAs coding for, in addition to xynA [Li et al. (1997) *Appl. Environ. Microbiol.* 63:628–635], celA [Li et al. (1997) *Appl. Environ. Microbiol.* 63:4721–4728], celB [Li et al. (1997) *Appl. Environ. Microbiol.* 63:628–635], celC [Li et al. (1997) *Appl. Environ. Microbiol.* 63:4721–4728], and celE [Chen et al. (1998) *FEMS Microbiol. Letts.* 159:63–68], three new sequences. One of the new sequences had an 800 bp insert (pBgl6), and its deduced amino acid sequence shared some homology with certain β-glucosidases. Using the cDNA fragment in pBgl6 as a hybridization probe, plaques containing cDNAs (pBgl13) with a complete ORF encoding a putative β-glucosidase (bglA) were isolated from the same cDNA library.

The complete nucleotide sequence of bglA (SEQ ID NO:1) is shown in Table 12. The total length of the cDNA was 2435 bp. It contained an ORF of 1974 bp (including the stop codon) encoding a polypeptide of 657 amino acids with a molecular mass of 75,227 Da (SEQ ID NO:2). Like cellulase B [Li et al. (1997) *Appl. Environ. Microbiol.* 63:628–635] and cellulase F isolated from the same fungus, there was a long 3' non-coding A-T rich end (423 bp) was observed after the ORF, but there was no apparent polyadenylation. The translation start codon (ATG) for bglA was assigned based on there being stop codons in all three frames preceding the ORF and there being no ATG codon upstream of the proposed ORF. In addition, the N-terminal region of BglA contains the properties of fungal signal peptides [von Heijne (1986) *Nucleic Acids Res.* 14:4683–4690]. Furthermore, close examination of the complete amino acid sequence of BglA revealed no NCRPD sequence, indicating that BglA is not a component of the HMWCs, and, surprisingly, that its cDNA was isolated due to non-specific cross-reaction between partial BglA and the NCRPD-specific antibodies.

Table 12 shows the nucleotide and deduced amino acid sequences of bglA from Orpinomyces sp. strain PC-2. N-terminal amino acid sequences of BglA and the two cell associated forms (Bgl1 and Bgl2) were underlined with dotted, single and double lines, respectively. The asterisk indicates the stop codon. See also SEQ ID NO:1, SEQ ID NO:2.

The G+C content of the entire cDNA and the ORF of bglA was 36% and 42.3%, respectively, and that of the 5' and 3' non-coding region was 9.1%, which is very low. Low G+C contents have also been found in other cDNAs of anaerobic fungi [Chen et al. (1997) *J. Bacteriol.* 179:6028–6034; Chen et al. (1998) *FEMS Microbiol. Letts.* 159:63–68; Li et al. (1997) *Appl. Environ. Microbiol.* 63:628–635].

The deduced amino acid sequence of BglA was compared with other protein sequences in the SWISS PROT and GP data banks. Comparisons using Bestfit program revealed that BglA had significant, but limited, levels of identity with β-glucosidases from *Cavia porcellus* (pig, 41.2%) [Hays et al. (1 996) *Biochem. J.* 319:829–837], *Costus speciosus* (40%) [Inoue et al. (1 996) *FEBS* 389:273–277], *Clostridium thermocellum* (40.2%) [Gräbnitz et al. (1991) *Eur. J. Biochem.* 200:301–309], *Bacillus circulans* (41.7%) [Paavilainen et al. (1993) *Appl. Environ. Microbiol.* 59:927–932], Thermoanaerobacter sp. (40.6%) [Breves et al.

(1997) *Appl. Environ. Microbiol.* 63:3902–3910], and *Thermotoga maritima* (40.7%) [Liebl et al. (1994) *Mol. Gen. Genet.* 242:111–115]. No significant identity (<20%) was found with β-glucosidases from aerobic fungi such as those from *Trichoderma reesei* and *Aspergillus aculeatus*. Multiple sequence alignment between BglA and structurally related β-glucosidases is given in Table 13. The sequences shown are the Orpinomyces sp. strain PC-2 (Bgla_Orpin), *Cavia porcellus* (Bgl_Capor) [Hays et al. (1996) *Biochem. J.* 319:829–837], *Costus speciosus* (Bgl_Cosspe) [Inoue et al. (1996) *FEBS* 389:273–277]; *Bacillus circulans* (Bgla_Bacci) [Paavilainen et al. (1993) *Appl. Environ. Microbiol.* 59:927–932]; *Thermotoga maritima* (Bgla_Thema) [Liebl et al. (1994) *Mol. Gen. Genet.* 242:111–115]; *Clostridium thermocellum* (Bgla_Clotm) [Gräbnitz et al. (1991) *Eur. J. Biochem.* 200:301–309] and *Thermoanaerobacter brockii* (Bgl_Theran) [Breves et al. (1997) *Appl. Environ. Microbiol.* 63:3902–3910]. Despite several homologous regions, BglA was much longer than its homologous enzymes. Close examination of the sequences revealed that Glu-250 and Glu-523 are conserved between all the enzymes and these two residues in the *Bacillus polymyxa* β-glucosidase were found to be directly involved in catalysis [Sanz-Aparicio et al. (1998) *J. Mol. Biol.* 275:491–502]. Gln82, His 260, Tyr 433, Glu-523 and Tyr 607, which are also conserved, have been identified as determinant residues for the recognition of substrates [Sanz-Aparicio et al. (1998) *J. Mol. Biol.* 275:491–502]. According to Henrissat and Bairoch [(1993) *Biochem. J.* 293:781–788], this group of enzymes was placed in Family 1 glycosyl hydrolases.

No β-glucosidase activity was found in the recombinant *E. coli* culture harboring the complete bglA cDNA. This is consistent with the failure to detect any positive plaques when using $^{4}$-methylumbelliferyl-β-D-glucoside, a fluorescent substrate of β-glucosidases, as a screening substrate. Lack of functional expression in *E. coli* might be related to differences between anaerobic fungi and *E. coli* in posttranslational modifications such as glycosylation and folding. We then attempted to express the gene in *S. cerevisiae*, because several other genes encoding hydrolytic enzymes have been expressed in various strains of the yeast. These include sequences encoding for two endoglucanases [Penttilä et al. (1987) *Yeast* 3:175–185], two cellobiohydrolases [Penttilä et al. (1988) *Gene* 63: 103–112] and one β-glucosidase from *Trichoderma reesei* [Cummings and Fowler (1996) *Curr. Genet.* 29:227–233], a xylanase from *Aureobasidlium pullulans* [Li and Ljungdahl (1996) *Appl. Environ. Microbiol.* 62:209–213], an α-amylase from wheat [Rothstein et al. (1987) *Gene* 55:353–356] etc. Recently, a cellulase gene cassette encoding the *Butyrivibrio fibrisolvens* endo-β-1,4-glucanase (END1), *Phanerochaete chrysosporium* cellobiohydrolase (CBH1), the *Ruminococcus flavefaciens* cellodextrinase (CEL1) and the *Endomyces fibrilizer* cellobiase (Bgl1) was successfully expressed in a laboratory strain of *S. cerevisiae* [Van Rensburg et al. (1998) *Yeast* 14:67–76].

Figures 2A, 2B:
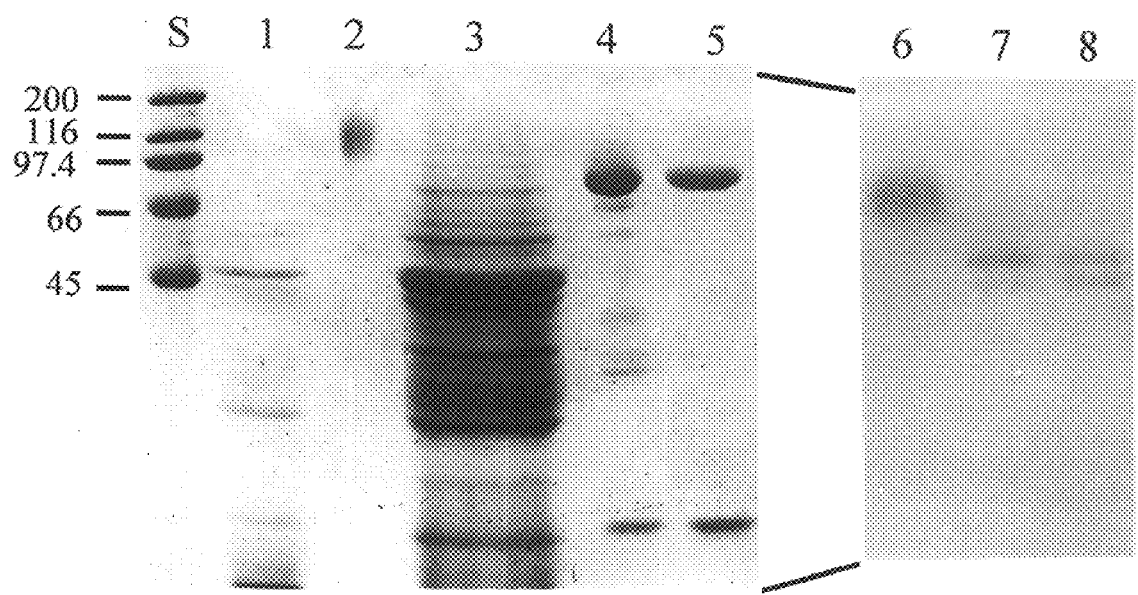
FIGS. 2A–2B show SDS-PAGE (10%)/zymogram analysis of the secreted and cell-associated forms of BglA.

After transformation, ten yeast transformants were grown in synthetic drop out supplement media without uracil, using raffinose as growth substrate and galactose as inducer (see Examples). β-glucosidase activity was measured for the cells and in the culture medium. All activity was found to be associated with cells, and no activity was found in the culture medium for all the transformants. It has been reported that culture conditions can strongly affect the secretion of enzymes from *S. cerevisiae*. For example, the secretion of a wheat α-amylase from *S. cerevisiae* into the medium was efficient only in a rich medium, but barely detectable in a minimal medium [Rothstein et al. (1987) *Gene* 55:353–356]. The secretion of the Orpinomyces BglA from *S. cerevisiae* is the same (FIG. 2). A substantial percent (40%) of the total β-glucosidase activity was found in the culture medium after 24 h of growth. The levels of activity in cell-associated and culture medium fractions stayed almost constant during the cultivation period (96 h). The growth rates for the transformants using plasmids with and without bglA inserted were the same, indicating that BglA and its gene did not affect the physiology of the yeast. A higher percentage of a *T. reesei* β-glucosidase, when expressed in *S. cerevisiae*, was found in the culture medium [Cummings and Fowler (1996) *Curr. Genet.* 29:227–233].

A summary of the purification of the Orpinomyces BglA secreted by *S. cerevisiae* culture is given in Table 1. The enzyme was purified about 28-fold to homogeneity with a specific activity of 18.8 U/mg and a yield of about 1%. Multiple peaks of activity were observed during the purification steps, but only the major activity peak was used for further purification, indicating that BglA was secreted into the culture medium with multiple forms due to proteolysis or different levels of glycosylation.

Figure 3:
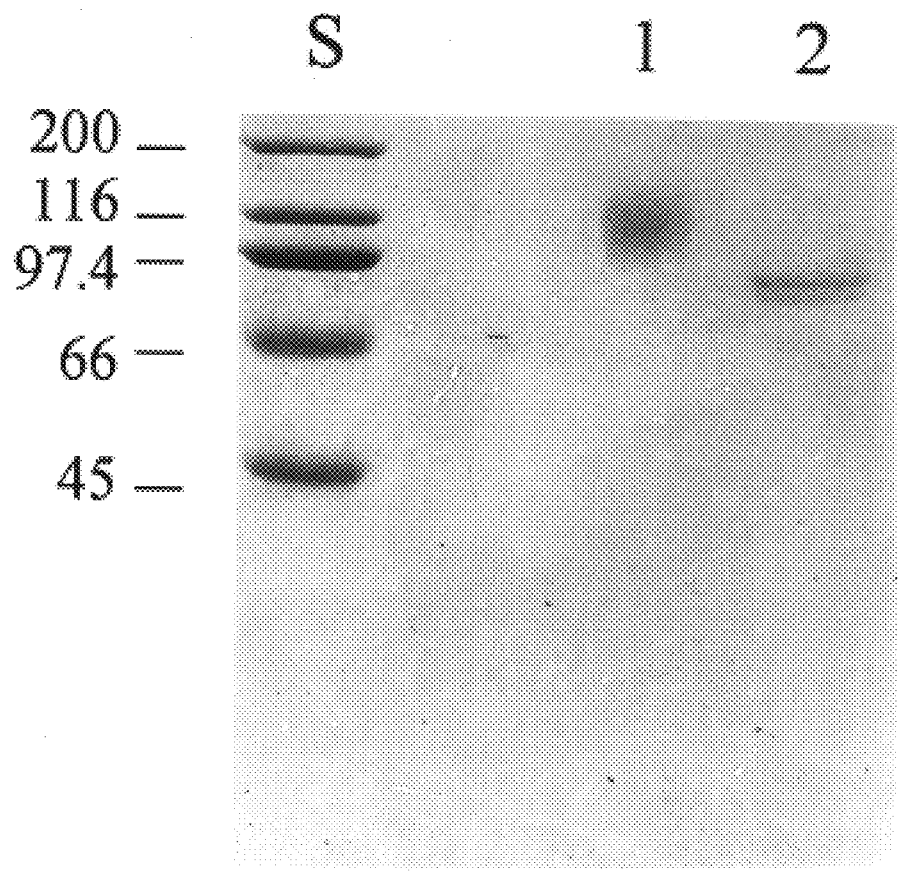
FIG. 3 illustrates SDS-PAGE Analysis of BglA treated with N-glycosidase F. Lane S, protein molecular mass standards; lane 1, purified secreted BglA (2.4 µg); lanes 2, purified secreted BglA (2.4 µg) treated with N-glycosidase F.

Two cell-associated forms (Bgl1 and Bgl2) of BglA were also partially purified from cell-free extracts of recombinant yeast cells using phenyl Sepharose, Mono Q and Superdex 200. The sizes of Bgl1 (first band in lanes 4 and 7) and Bgl2 (first band in lanes 5 and 8) were estimated to be around 65 kDa by SDS-PAGE/zymogram analysis (FIGS. 3A–3B).

Figure 4B:
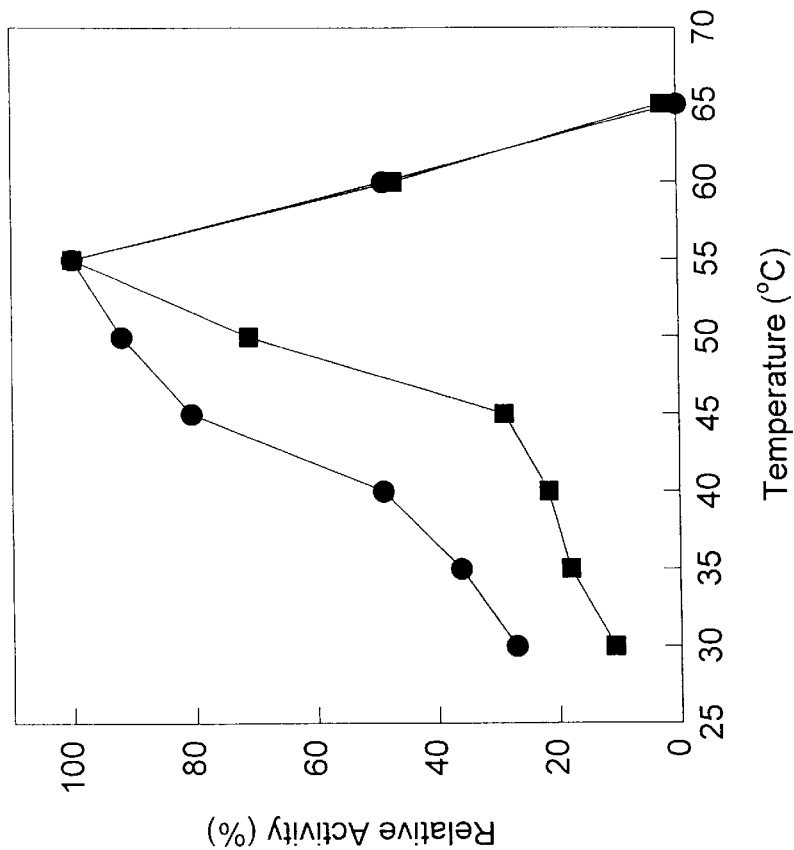
FIGS. 4A–4B show the effects of pH and temperature on the activity of purified BglA.
Figure 4A:
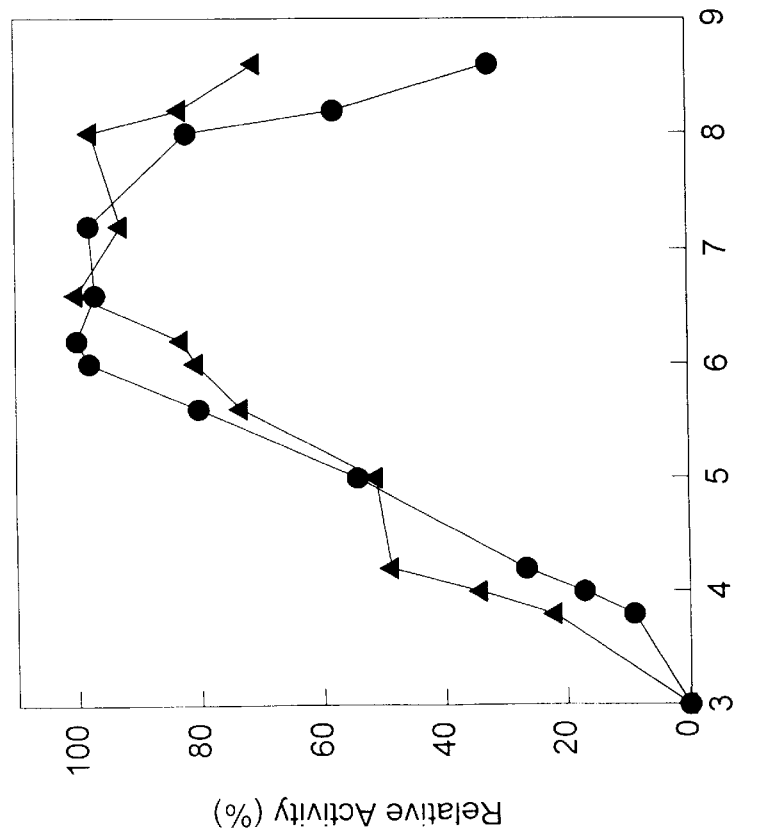

The purified BglA, Bgl1 and Bgl2 were all subjected to N-terminal amino acid sequencing. The secreted BglA had an N-terminal sequence of KKCIVKSDAA (SEQ ID NO:3), which matched amino acid residues 17–26 (Table 12), demonstrating that amino acid residues 1–16 were cleaved during secretion. Thus, the first 16 amino acid residues apparently serve as a signal peptide in both Orpinomyces and *S. cerevisiae*. Removal of 16 amino acid residues at the N-terminus resulted in 641 amino acid residues with a calculated mass of 73,608 Da for the mature BglA. The signal peptide had a basic amino acid (Lys) as the second N-terminal residue, followed by a hydrophobic amino acid region containing in some points non-hydrophobic residues. This is in agreement with the work of Ngsee et al. [Ngsee et al. (1989) *Mol. Cell. Biol.* 9:3400–3410], where using site-directed mutagenesis of the signal sequence of yeast invertase gene, suc 2, it was showed that the essential feature of a signal peptide for yeast is a hydrophobic core of 6–15 amino acids. The core region can be interrupted to a certain extent by non-hydrophobic residues. The purified recombinant BglA gave a broad band with a average size of about 110 kDa on SDS-PAGE (FIG. 3A), which was larger than that calculated for the deduced mature enzyme. Only one N-glycosylation site Asn-X-Ser/Thr [Orlean et al. (1991) *Methods Enzymol.* 194:682–696] corresponding to amino acid residues 280–282 (Table 12) was found in the entire BglA sequence. However, the size of the purified enzyme after treated with N-glycosidase F, an enzyme specifically removing N-glycosylation, shifted to two sharp bands with very similar sizes (87 and 92kDa) on SDS-PAGE (FIG. 4). N-terminal amino acid sequencing revealed that these two bands had amino acid sequences at their N-termini identical to that of the secreted BglA. These results indicate that about 20% (wt/wt) of N-glycosylation was added to BglA during secretion from *S. cerevisiae* and that the size difference between the two similar bands after the N-glycosidase F treatment is probably due to O-glycosylation. The β-glucosidase purified from the culture supernatant of the same fungus had a mass of 85 kDa including 8.5% (wt/wt) carbohydrate [Chen et al. (1994) *Appl. Environ. Microbiol.*

60:64–70]. If the native β-glucosidase [Chen et al. (1994) supra] and the secreted BglA reported here are products of the same gene, bglA of Orpinomyces PC-2, much heavier glycosylation (hyperglycosylation) was put by *S. cerevisiae* than by Orpinomyces. Hyperglycosylation was also found on the *T. reesei* endoglucanases [Penttilä et al. (1987) *Yeast* 3:175–185], cellobiohydrolases [Penttilä et al. (1988) *Gene* 63:103–112] and β-glucosidase [Cummings and Fowler (1996) *Curr. Genet.* 29:227–233] expressed in and secreted from *S. cerevisiae*.

The N-terminal sequence for Bgl1 was APEDSGVES (SEQ ID NO:4) that matched amino acid residues 40–48, while that of Bgl2, GEDDELLDLS (SEQ ID NO:5) corresponding to amino acid residues 49–58 (Table 12). Thus the cleavages resulted in two truncated forms (Bgl1 and Bgl2) of BglA (FIGS. 3A–3B). These results indicate that Bgl1 and Bgl2 were cleaved at wrong (or alternate) sites and subsequently trapped during transport in the secretory pathway. The fact that these two truncated forms retained catalytic function indicates that the sequence of the BglA protein up to amino acid residue 48 is not critical for catalysis. Without wishing to be bound by theory, it is believed that this is why this region is absent in the homologous bacterial β-glucosidases (FIG. 1).

Figure 5:
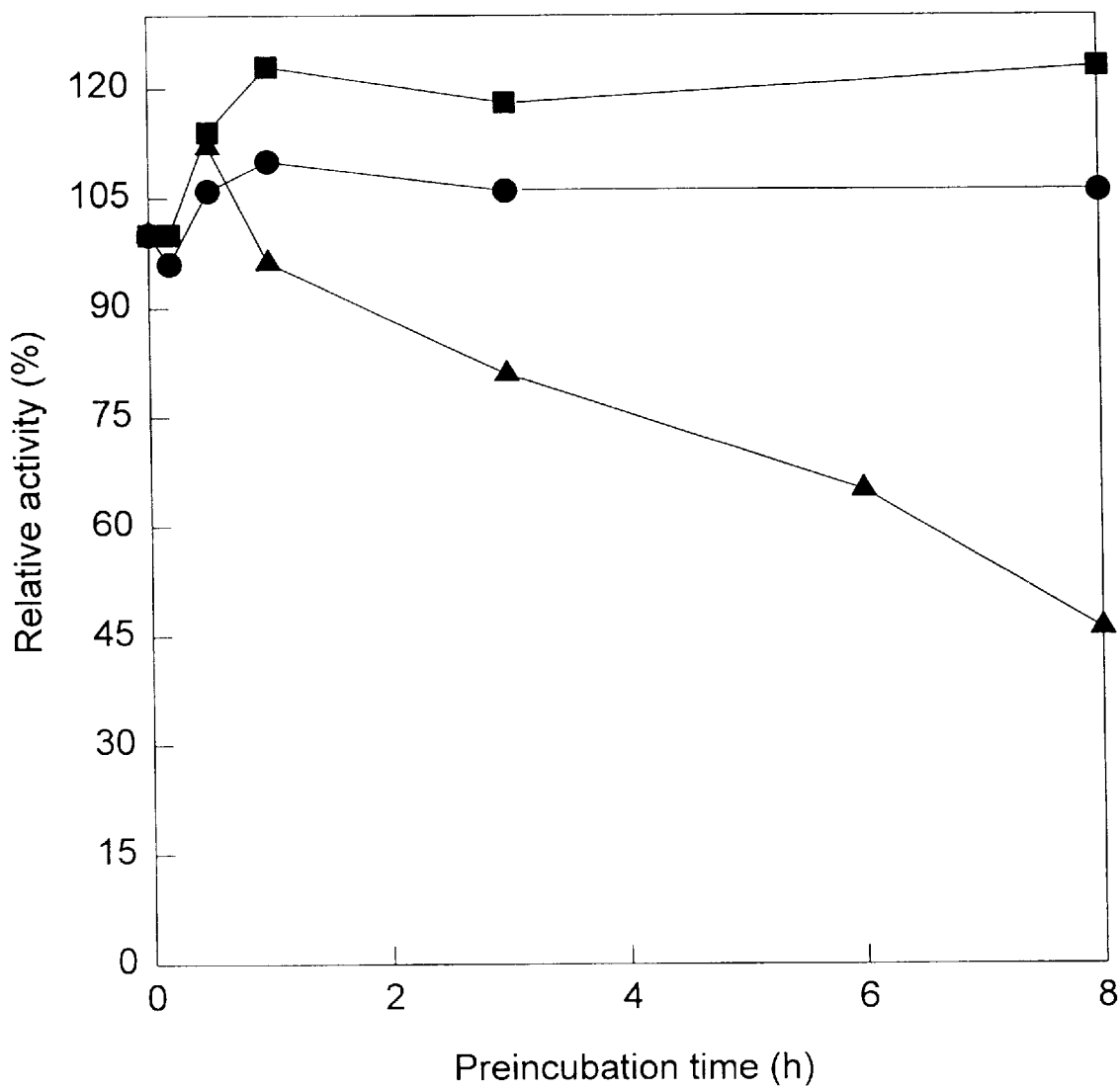
FIG. 5 illustrates the thermostability of purified BglA and BglA treated with N-glycosidase F. The enzyme was incubated at 40° C. (●), 50° C. (■) and 55° C. (▲).

The catalytic properties of the Orpinomyces PC-2 β-glucosidase were determined. Activity of the purified secreted BglA against ρNPG and cellobiose was determined from pH 3.8 to 8.6 at 40° C. The optimum pH with both substrates was found to be between 5.5–7.5 (FIG. 5; Table 2). The enzyme was stable for at least 24 h between pH 3.4 to 10.2 at 4° C. Hydrolysis of ρNPG and cellobiose by BglA, determined in 50 mM sodium phosphate buffer, pH 6.0, was most active at 55° C. (FIG. 5; Table 2). Enzyme activity decreased rapidly above 60° C. and lost its activity at 65° C. The enzyme maintained 100% of its activity for 8 h at 40 and 50° C. (FIG. 6). Inactivation of BglA occurred slowly at 55° C., with 50% of the enzyme activity remaining after 8 h of incubation (FIG. 6). At 60° C. the enzyme was quickly inactivated. The optimum pH and temperature ranges of the recombinant BglA are similar to those reported for the native β-glucosidases of Orpinomyces sp strain PC-2 [Chen et al. (1994) *Appl. Environ. Microbiol.* 60:64–70], *N. frontalis* [Herbaud and Fevre (1990) *Appl. Environ. Microbiol.* 56:3164–3169], and Piromyces sp. strain E2 [Teunissen et al. (1992) *Arch. Microbiol.* 158:276–281].

$K_m$, $K_i$, and $V_{max}$ values for the secreted BglA were obtained from Lineweaver-Burk plots (Table 2). The $K_m$ value with ρNPG as substrate at 40° C. and pH 6.0 was found to be 0.762 mM, higher than that [0.35 mM; Chen et al. (1994) *Appl. Environ. Microbiol.* 60:64–70] reported for the native β-glucosidase of the same fungus. However, the $K_m$ value with cellobiose as substrate, 0.31 mM, was very similar to that (0.25 mM) for the native β-glucosidase. These values are within the range of $K_m$ values reported for several β-glucosidases of anaerobic fungi [Herbaud and Fevre (1990) *Appl. Environ. Microbiol.* 56:3164–3169; Li and Calza (1991A) *Enzyme Microb. Technol.* 13:622–628; Li and Calza (1991B) *Biochem. Biophys. Acta* 1080:148–154; Teunissen et al. (1992) *Arch. Microbiol.* 158:276–281]. Comparison between the $K_m$ values for β-glucosidases from various sources indicates that the ones from anaerobic fungi have lower $K_m$ values than those from bacteria or aerobic fungi. The differences of $K_m$ values between the Orpinomyces native β-glucosidase and the recombinant BglA could be due to the different levels of glycosylation. Ward reported that chymosin, when a site for N-glycosylation was introduced, had lower specific activity [Ward (1989) EMBO-ALKO Workshop on Molecular Biology of Filamentous Fungi. Foundation for Biotechnical and Industrial Fermentation Research, Nevalainen, H. and Pentillä, M. (Eds), Espoo, pp. 119–128]. The effect on specific activity was considered to be probable a consequence of active site change by the glycosylation [Archer and Peberdy (1997) *Critical Rev. Biotechnol.* 17:273–306; Ward (1989) EMBO-ALKO Workshop on Molecular Biology of Filamentous Fungi. Foundation for Biotechnical and Industrial Fermentation Research, Nevalainen, H. and Pentillä, M. (Eds), Espoo, pp. 119–128].

Glucose and glucono-1,5-lactone competitively inhibited BglA with Ki of 3.6 and 0.05 mM, respectively. These numbers are lower than those for the native Orpinomyces β-glucosidase. Withing wishing to be bound by theory, it is believed that this is due to glycosylation. The hydrolysis rates of BglA went down with high concentrations of substrate, particularly cellobiose (e.g. more than 1.5 mM). Substrate inhibition is common for β-glucosidases [Chen et al. (1994) *Appl. Environ. Microbiol.* 60:64–70; Li and Calza (1991 A) *Enzyme Microb. Technol.* 13:622–628; Li and Calza (1991B) *Biochem. Biophys. Acta* 1080:148–154] and is attributed to retention of product on the enzyme [Li and Calza (1991 B) *Biochem. Biophys. Acta* 1080:148–154].

BglA has specificity for aryl-β-glucoside bonds and was not able to hydrolyze alkyl-β-glucoside bonds or α-1,4-glucoside bonds. The enzyme rapidly hydrolyzed sophorose (β-1,2-glucobiose), laminaribiose (β-1,3-glucobiose) and cellobiose (β-1,4-glucobiose), but lacked activity on gentibiose (β-1,6-glucobiose), methyl-β-glucoside, ρ-nitrophenyl-β-xyloside (ρNPX), salicin, maltose, sucrose, lactose, xylan, microcrystalline cellulose, or carboxymethyl cellulose. Low level of activity was found on ρNPX when enzyme in the assay was increased 20 times. BglA reported here and the native β-glucosidase [Chen et al. (1994) *Appl. Environ. Microbiol.* 60:64–70] had the almost identical substrate specificity. Interestingly, such substrate specificity is very similar to that of a β-glucosidase purified from the anaerobic rumen bacterium *Ruminococcus albus* [Ohmiya et al. (1985) *J. Bacteriol.* 161:432–434].

To compare enzyme activities of crude enzyme preparations, 750 ml of *T. reesei* supernatant was concentrated about 56 fold to 13.5 ml. Under standard assay conditions, activities of CMCase, FPA, and β-glucosidase of the sample are given in Table 1. CMCase and FPA activities of the cell-free extract of the recombinant Orpinomyces CelF (cellobiohydrolase II-like cellulase) are 8.43 U/ml and 0.46 U/ml, respectively. CelF did not have any detectable activity against pNPG. One hundred ml yeast culture medium containing the recombinant Orpinomyces β-glucosidase (Bgal) was concentrated about 10 fold to 10 ml. Glucosidase activity in the sample was 1.68 U/ml with pNPG as substrate. The recombinant β-glucosidase did not hydrolyze CMC, filter paper, or Avicel.

Hydrolysis products formed during the action of various combinations of the enzyme samples on filter paper were characterized. Reactions (1.5 ml) containing 4 μl of concentrated *T. reesei* cellulase (0.054 U of FPA), and/or 10 μl Orpinomyces recombinant CelF (0.0046 U of FPA), and 24 μl recombinant β-glucosidase were incubated at 50° C. for I and 3 h. The hydrolysis products formed were determined by HPLC (Table 5).

The hydrolysis products formed during the action of various combinations of the enzyme samples on Avicel were characterized. Reactions (1.5 ml) containing 8 μl concentrated *T. reesei* cellulase (0.108 U of FPA), and/or 20 μl Orpinomyces recombinant CelF (0.0092 U of FPA), and/or 24 μl recombinant β-glucosidase were incubated at 37° C. for 16 h in a shaker (280 rpm). The hydrolysis products formed were determined by HPLC (Table 6).

The hydrolysis products formed during the action of various combinations of the enzyme samples on CMC were characterized. Reactions (1.5 ml) containing 0.2 μl concentrated T. reesei cellulase (0.0054 U of FPA), and/or 10 μl Orpinomyces recombinant CelF (0.0046 U of FPA), and/or 6 μl recombinant β-glucosidase were incubated at 50° C. for 0.5 and 2 h. The hydrolysis products formed were determined by HPLC (Table 7).

Hydrolysis products formed during the action of various combinations of the enzyme samples on corn fiber were characterized. 1.5 ml reaction volume containing 10 μl of concentrated T. reesei cellulase (0.136U of FPA), and/or 20 μl of the recombinant CelF of Orpinomyces PC-2 (0.0092 U of FPA), and/or 20 μl of the recombinant BglOr, and 50 mg corn fiber was incubated at 40° C. for 12 h. The hydrolysis products formed were determined by HPLC (Table 8).

Glucose production by T. reesei cellulase supplemented with recombinant β-glucosidase of Orpinomyces PC-2 or β-glucosidase of Aspergillus niger using Avicel as a substrate was compared. A 1.5 ml reaction volume containing 8 μl of concentrated T. reesei cellulase (0.108 U of FPA), 20 μl the recombinant of CelF of Orpinomyces PC-2 (0.0092 U of FPA), various amounts of the β-glucosidases, and 15 mg Avicel was incubated at 40° C. for 12 h in a shaker (280 rpm). The hydrolysis products formed were determined by HPLC (Table 9).

Glucose production by T. reesei cellulase supplemented with recombinant β-glucosidases of Orpinomyces PC-2 and Aspergillus niger was compared using filter paper as the substrate. A 1.5 ml reaction volume containing 4 μl of concentrated T. reesei cellulase (0.054 U of FPA), 10 μl recombinant CelF of Orpinomyces PC-2 (0.0046 U of FPA), and 20 μl of the recombinant BglOr or BglAn from Aspergillus niger was incubated at 50° C. for 1 and 3 h, respectively. The hydrolysis products formed were determined by HPLC (Table 10). Because the present Orpinomyces PC-2 stimulated saccharification by T. reesei enzymes, it is desirable to produce recombinant T. reesei expressing the Orpinomyces β-glucosidase for improved cellulase-to-glucose conversion.

In recent years, with the realization of β-glucosidase's critical role in cellulolytic enzyme systems, much research effort has been directed toward finding a suitable β-glucosidase for application in the enzymatic conversion of cellulose to glucose [Saha et al. (1995) In Enzymatic Degradation of Insoluble Carbohydrates, Eds. Saddler and Penner, M. H. ACS Symposium Serious 618, pp.197–207]. Many attempts have been made to increase glucose production by the supplementation of exogenous β-glucosidase in cellulose hydrolysis processes using cellulase enzymes [Saha et al. (1995) In Enzymatic Degradation of Insoluble Carbohydrates, Eds. Saddler and Penner, M. H. ACS Symposium Serious 618, pp.197–207; Desrochers et al. (1981) Appl. Environ. Microbiol. 41:222–228]. Several are outlined here: Varying concentrations of Aspergillus niger β-glucosidase were mixed with T. reesei cellulase, leading to a 20% increase in conversion of cellulose to ethanol in 24 h on simultaneous saccharification and fermentation (SSF) [Pemberton et al. (1980) Can. J. Chem. Eng. 58:723–734]. The β-glucosidase from Aureobasidium pullulans showed a synergistic interaction with cellulase to increase glucose production by 13.5% [Saha et al. (1995) In Enzymatic Degradation of Insoluble Carbohydrates, Eds. Saddler and Penner, M. H. ACS Symposium Serious 618, pp.197–207]. The addition of a cloned glucosidase from Clostridium thermocellum increased the degradation of crystalline cellulose by the C. thermocellum cellulase complex [Katayeva et al. (1992) Enzyme Microb. Technol. 14:407–412]. However, the increase in glucose production was not very significant, and therefore better β-glucosidases with high specific activity and low product inhibition are urgently needed.

Inhibition by glucose, a common characteristic of β-glucosidases, is an obvious constraint to be overcome for this enzyme to have industrial applications. Most β-glucosidases studied were competitively inhibited by glucose. Some glucose inhibition constants for β-glucosidases from various sources are shown in Table 8. β-Glucosidase from T. reesei is more sensitive to glucose inhibition (Ki, 0.62 mM), while the Orpinomyces β-glucosidase is much less sensitive (Ki, 8.75 mM). This could be why the increase of glucose production is so substantial when the Orpinomyces β-glucosidase is added to the T. reesei cellulase preparation during cellulose hydrolysis. The Orpinomyces β-glucosidase converted the accumulated cellobiose and other cello-oligosaccharides to glucose, which could not be achieved by the Trichoderma β-glucosidase due to inhibition by relatively low concentrations of glucose. The total amount of glucose in the presence of Orpinomyces β-glucosidase is 7 fold higher, which is more than the total moles of glucose and cellobiose together without supplementation, indicating that conversion of cellobiose to glucose greatly eliminates the cellobiose inhibition on Trichoderma endoglucanases and cellobiohydrolases. This was also true when corn fiber was the substrate, where cellobiose accumulated with T. reesei cellulase alone and Orpinomyces β-glucosidase converted the cellobiose completely to glucose.

In comparison to β-glucosidase from A. niger, β-glucosidase from Orpinomyces PC-2 was significantly more efficient in increasing glucose production when added to cellulose hydrolysis using T. reesei cellulases. Based on the data obtained using Avicel as substrate, β-glucosidase from Orpinomyces was four times more effective in catalyzing glucose production than the Aspergillus β-glucosidase.

Our results demonstrate that β-glucosidase from the anaerobic fungus Orpinomyces PC-2 is superior to other glucosidases from fungi and bacteria. The high specific activity, low Km, and high Ki by glucose, and activity toward cello-oligosaccharides up to pento-oligosaccharide [Chen et al. (1994) Appl. Environ. Microbiol. 60:64–70] should make the enzyme a suitable candidate for application in the hydrolysis of cellulose to glucose.

It will further be understood by those skilled in the art that other nucleic acid sequences besides that disclosed herein for BglA will function as coding sequences synonymous with the exemplified coding sequences. Nucleic acid sequences are synonymous if the amino acid sequences encoded by those nucleic acid sequences are the same. The degeneracy of the genetic code is well known to the art. For many amino acids, there is more than one nucleotide triplet which serves as the codon for a particular amino acid, and one of ordinary skill in the art understands nucleotide or codon substitutions which do not affect the amino acid(s) encoded. It is further understood in the art that codon substitutions to conform to common codon usage in a particular recombinant host cell is sometimes desirable Specifically included in this invention are sequences from other strains of Orpinomyces and from other anaerobic fungi which hybridize to the sequence disclosed for β-glucosidase under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences, (indicating about 95–100% nucleotide sequence identity). Also specifically included in this invention are sequences from other strains of Orpinomyces species and other anaerobic fungi which hybridize to the sequences disclosed for bglA under moderately stringent conditions. Moderately stringent conditions refer to conditions understood in the art for a given probe sequence and "conditions of medium stringency" means hybridization and wash conditions of 50°–65° C., 1×SSC and 0.1% SDS (indicating about 80–95% similarity). Also specifically included in this invention are sequences from other strains of Orpinomyces from other anaerobic fungi, and from other organisms, including humans, which hybridize to the sequences disclosed for bglA under highly stringent conditions. Highly stringent conditions refer to conditions understood in the art for a given probe sequence and "conditions of high stringency" means hybridization and wash conditions of 65°–68° C., 0.1×SSC and 0. 1% SDS (indicating about 95–100% similarity). Hybridization assays and conditions are further described in Sambrook et al. [(1989) supra].

A method for identifying other nucleic acids encoding β-glucosidases is also provided wherein nucleic acid molecules encoding β-glucosidases are isolated from an anaerobic fungus, and nucleic acid hybridization is performed with the nucleic acid molecules and a labeled probe having a nucleotide sequence that includes all or part of nucleotide sequence SEQ ID NO:1. By this method, silencing genes similar to the exemplified bglA gene may be identified and isolated from other strains of Orpinomyces or other anaerobic fungi. All or part of a nucleotide sequence refers specifically to all continuous nucleotides of a nucleotide sequence, or e.g. 1000 continuous nucleotides, 500 continuous nucleotides, 100 continuous nucleotides, 25 continuous nucleotides, and 15 continuous nucleotides.

Sequences included in this invention are those amino acid sequences which are 75% identical to the amino acid sequences encoded by the exemplified Orpinomyces PC-2 bglA. Sequences included in this invention are also those amino acid sequences which are 80, 85, 90, 95 to 100%, and all integers between 75% and 100%, identical to the amino acid sequences encoded by exemplified Orpinomyces bglA, SEQ ID NO:2, amino acids 1–641, 24 to 641 or 33 to 641.

It is well-known in the biological arts that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pp. 345–352, which is incorporated by reference herein provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Percentage of sequence identity for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information), or by inspection. Sequences are typically compared using either BlastN or BlastX with default parameters.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Sequences are preferably compared to a reference sequence using GAP using default parameters.

Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that polynucleotide sequences are substantially identical is if two molecules selectively hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically stringent conditions for a Southern blot protocol involve washing at 65° C. with 0.2×SSC.

Monoclonal or polyclonal antibodies, preferably monoclonal, specifically reacting with a particular β-glucosidase enzyme of the present invention may be made by methods known in the art. See, e.g., Harlow and Lane

[(1988) *Antibodies: A Laboratory Manual*, Cold Spring Harbor Laboratories; Goding (1986) *Monoclonal Antibodies: Principles and Practice*, 2d ed., Academic Press, New York].

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. [(1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York]. Abbreviations and nomenclature, where employed, are deemed standard in the field and commonly used in professional journals such as those cited herein.

Each reference cited in the present application is incorporated by reference herein to the extent that it is not inconsistent with the present disclosure.

The following examples are provided for illustrative purposes, and is not intended to limit the scope of the invention as claimed herein. Any variations in the exemplified articles which occur to the skilled artisan are intended to fall within the scope of the present invention.

EXAMPLES

Example 1

Strains, Enzymes, Plasmids and Genes

*Escherichia coli* TOP10, *S. cerevisiae* INSC1 (MAT α his 3-D 1 El 2 trpl-289 ura3-52) and plasmid pYES2 were purchased from Invitrogen Corp. (San Diego, Calif.). pYES2 possesses ampicillin and tetracycline resistance genes for selection in *E. coli*, a URA3 gene for high-copy-number maintenance and selection in *S. cerevisiae* INSC1, and a GAL 1 promoter sequence. The bglA cDNA of Orpinomyces sp. PC-2 was cloned by screening a cDNA library [Chen et al. (1995) *Proc. Natl. Acad. Sci. USA* 92:2587–2591] as described below.

A culture of *T. reesei* was grown at 23° C. for 4–5 days on 3% Avicel with 0.5% wheat bran in enriched Mandels minimal solution [Mandels and Andreotti (1978) *Process Biochem.* 5:6] plus 50 mM sodium citrate (pH 5.0) in 2 L flasks. The culture was centrifuged at 15,000 g for 15 min to remove residual wheat bran, and fungal mycelia. A crude enzyme preparation from the culture supernatant was obtained by ultrafiltration using an Amicon Stircell equipped with a PM 10 membrane (10 kDa) and stored at −20° C. until used.

A single colony of *E. coli* XL-1 Blue harboring pCEL8 grown on a LB-ampicillin plate was inoculated into a flask containing 500 ml of LB-ampicillin liquid medium. The culture was shaken (280 rpm) at 37° C. and grown to an $OD_{600}$ of approximately 1.0. Isopropyl-1-thio-β-D-galactopyranoside (1 mM) was added and the culture was shaken for another 4 h to induce and allow expression. Cells were harvested by centrifugation (5,000×g, 10 min), washed with 50 ml of buffer containing 50 mM sodium citrate (pH 5.5) and re-suspended in 30 ml of the same buffer. The cells were then disrupted by sonication (four times at 7,000 cycles in a Branson Sonifier 450). Cell debris were removed by centrifugation (15,000×g, 10 min).

Aspergillus β-Glucosidase was purchased from Fluka Chemie AG (Switzerland).

Example 2

Screening of an Orpinomyces cDNA Library Using Antibodies

The production of antibodies against the different regions of Orpinomyces xylanase A was described previously [Li et al. (1997) *Appl. Environ. Microbiol.* 63:628–635]. Immunoscreening was done following the procedure of Pico Blue™ Immunoscreening kit (Stratagene, La Jolla, Calif.). Pure positive plaques were obtained after a secondary screening. Lambda phages were converted into pBluescript SK- by in vivo excision and the pBluescript DNA was purified from overnight grown cultures in Luria-Bertani medium containing 50 μg/ml ampicillin using the plasmid purification system purchased from Qiagen (Chatsworth, Calif.). DNA sequence was determined by automatic PCR sequencing [Li et al. (1997) *Appl. Environ. Microbiol.* 63:628–635].

The nucleotide sequence of Orpinomyces PC-2 BglA has been assigned accession number AF016864 in the GenBank database.

Example 3

DNA Hybridization Screening

A 400-bp DNA fragment of the partial bglA sequence obtained by antibody screening was amplified by PCR and labeled with digoxigenin. Using the labeled fragment as a hybridization probe, the same cDNA library was screened according to instructions of Boehringer Mannheim (Indianapolis, Ind.) using the Genius kit. Positive plaques were converted to pBluescripts, and their inserted DNA sequences were determined as described [Li et al. (1997) *Appl. Environ. Microbiol.* 63:628–635].

Example 4

Construction of Plasmid Cassette

Plasmid pYES2 was digested with SacI and XbaI overnight. The digested plasmid was purified using the Geneclean II kit (Bio 101, Inc., La Jolla, Calif.). On the basis of the nucleotide sequence of the cloned gene, forward (PFBg1, 5'GCCGAGCTCGATGAAGACTCTTACTGTTTTC3') (SEQ ID NO:6) and reverse (PRBg1, 5'GCTCTAGAGTTAGTTTTGTTCAACATTTTC3') (SEQ ID NO:7) primers were synthesized. PFBgl corresponded to the first seven amino acids of the open reading frame (ORF) and had a SacI site attached, whereas PRBgl corresponded to the last six amino acids plus a stop codon and had a XbaI site attached. Using PFBgl and PRBgl as primers and plasmid PBgl13 as template, the whole ORF was amplified by PCR. PCR was carried out for 30 cycles of denaturation (1 min at 94° C.), annealing (1.5 min at 42° C.) and extension (3.5 min at 72° C.) on a 480 Thermocycler (Perkin-Elmer Co., Norwalk, Conn.). PCR products were purified using the Geneclean kit and digested with SacI and XbaI. Digested DNA fragments were purified and concentrated before they were ligated to the digested pYES2 with T4 ligase.

Example 5

Transformation of E. Coli and Plasmid Propagation

Ligation reactions were performed using a rapid ligation kit (Boehringer Mannheim). E. coli TOP10 transformants were plated out on Luria-Bertani plates containing ampicillin (50 μg/ml). Colonies were picked up and grown overnight in Luria-Bertani liquid medium containing ampicillin. Plasmids were purified with the spin column kit from Qiagen. Restriction digestion and nucleotide sequencing were employed to verify the presence, orientation and sequence of the insert.

Example 6

Transformation of S. Cerevisiae and Expression

A single colony of yeast strain INVSc1 was grown to an $OD_{600}$ of 1.3 in YPD medium, pH 6.5, containing 1% (wt/vol) yeast extract, 1% (wt/vol) bactopeptone and 1% (wt/vol) dextrose. Cells were harvested by centrifugation (4,000×g for 5 min) at 4° C. and washed twice with ice-cold sterile $H_2O$ and twice with ice-cold 1M sterile sorbitol. After that, the cells were resuspended in 0.5 ml of 1M sorbitol. Approximately 5 μg of plasmids was used to transform 40 μl of prepared yeast cells using an electroporator (Bio-Rad Laboratories, Hercules, Calif.). Transformants were grown on DOB medium containing 0.17% (wt/vol) yeast nitrogen base without amino acids and $NH_2SO_4$, 2.0% (wt/vol) dextrose, 0.08% (wt/vol) drop out supplements lacking uracil (Bio101, Inc.), 2% (wt/vol) agarose and 1M sorbitol. The plates were incubated at 30° C. for 3 to 5 days.

Ten putative transformants were chosen for induction experiments. Each was cultivated in 10 ml of DOB medium containing 0.17% (wt/vol) yeast nitrogen base without amino acids and $NH_2SO_4$, 0.08% (wt/vol) drop-out supplement lacking uracil and 4% (wt/vol) raffinose. After the $OD_{600}$ reached 1.0, galactose was added to a final concentration of 2% (wt/vol). Samples were collected before and periodically after the addition of galactose. Transformant #7, which produced the highest level of β-glucosidase activity, was chosen for induction experiments in a more nutritious medium. A single colony of the transformant was used for inoculating 2 ml of DOB medium. After $OD_{600}$ reached 0.8, one milliliter of the culture was added to 100 ml YPD-raffinose (4% wt/vol) medium, and the culture was shaken (250 rpm) at 30° C. Sterile galactose (2.0%, wt/vol) was added to the culture after $OD_{600}$ reached 1.0. Samples were collected before and periodically after the addition of galactose. Cells were harvested by centrifugation (5,000×g, 5 min) at 4° C. All samples were kept at −20° C. until analyzed.

Yeast strain INSC1 harboring plasmid p69 (pYES inserted with BglA cDNA) was cultivated in a medium containing 4% raffinose for 20 h until an $OD_{600}$ of 1.0 was reached. Then sterile galactose was added to 2.0% and the culture was shaken for another 24 h. The yeast cells were removed by centrifugation (5,000×g, 20) and supernatant was concentrated using the method described above. The concentrated sample was stored at −20° C.

Example 7

Enzyme Assays

β-Glucosidase (p-nitrophenyl-β-D-glucosidase [pNPGase]) and cellobiase activities were determined by the following standard procedures. With p-nitrophenyl-β-D-glucoside (pNPG) as the substrate, the reaction mixture of 1.2 ml contained 0.3 ml of appropriately diluted enzyme solution, 0.6 ml of 50 mM sodium phosphate buffer, pH 6.0, and 0.3 ml of 12 mM pNPG. The reaction was carried out for 10 min at 40° C. and stopped by the addition of 2.4 ml of 1M $Na_2CO_3$. The liberated p-nitrophenol was measured spectrophotometrically at 405 nm [Herr et al. (1978) Appl. Microbiol. Biotechnol. 5:29–36; Chen et al. (1992) Biochem. Biophys. Acta. 1121:54–60]. Cellobiase activity was determined by using a reaction mixture of 2 ml containing 1 ml of appropriately diluted enzyme solution in 50 mM sodium phosphate buffer, pH 6.0, and 1 ml of 2 mM cellobiose. The reaction was carried out at 40° C. for 30 min and was stopped by placing the assay tubes in boiling water for 5 min. Liberated glucose was measured with a glucose determination kit (Sigma Chemical Co., St. Louis, Mo.) according to the manufacturer's instructions. One unit of β-glucosidase or cellobiase activity is defined as the amount of enzyme required to hydrolyze 1 μmole of substrate per min. Specific activity is expressed as unit per milligram of protein.

Cellobiase activity was determined using a reaction mixture of 2 ml containing 1 ml appropriately diluted enzyme solution in sodium phosphate, 50 mM, pH 6.0, and 1 ml cellobiose, 2 mM. The reaction was carried out at 50° C. for 30 min and stopped by placing the assay tubes in boiling water for 5 min. Liberated glucose was measured with the glucose determination Kit No 510 (Sigma) according to the manufacturer's instruction.

Avicel activity and carboxymethylcellulase activity (CMCase) were measured in 50 mM citrate phosphate, pH 5.5. A volume of 1.0 ml Avicel suspension (1.5%) or carboxymethylcellulose (CMC, 1%) was incubated at 50° C. with 0.5 ml suitable diluted enzyme solution for 4 and 0.5 h, respectively. The concentration of reducing sugar in the supernatant was determined with the dinitrosalicyclic acid reagent [Miller (1959) Anal. Chem. 31:426–428]. To assay filter paper activity (FPA) assay, a 50 mg Whatman No. 1 filter paper strip was used as substrate in the reaction for 1 h. One unit (U) of enzyme activity was defined as the amount of enzyme required for the release of one μmol of product per min under assay conditions. Specific activity was expressed as units per mg of protein.

To examine hydrolysis of filter paper by mixed culture filtrates, a total reaction volume of 1.5 ml contained 50 mg filter paper (50 mM citrate phosphate, pH 5.4), suitable amount of a diluted T. reesei cellulase preparation, the Orpinomyces recombinant CelF, β-glucosidase, and Aspergillus β-glucosidase. The reactions were stopped by boiling for 5 min. The cello-oligosaccharides or other monosugars in the reaction mixtures were determined using a HPLC method (see below). Similar procedures were employed when Avicel, CMC, and corn fiber were used as substrates.

HPLC analysis was used to examine the hydrolysis products of various enzyme reactions. Cello-oligosaccharides or various monosugars released from the substrates were analyzed with a Hewlett-Packard 1100 series HPLC equipped with an autoinjector and a 1047A RI detector using a Bio-Rad Aminex HPX-42A or HPX-87P carbohydrate columns. Water was used as the mobile phase at a flow rate of 0.6 ml/min and the column temperature was set at 80° C. Glucose, cellobiose, cellotriose, cellotetraose, and cellopentaose or cellobiose, glucose, xylose, galactose, arabinose, and mannose were used as standards.

Example 8

Enzyme Purification

*S. cerevisiae* culture (7.5 liter) harboring PBgl13 was grown in YPD medium containing 4% raffinose for 24 h at 30° C. The culture supernatant was obtained by centrifugation (4,000×g, 20 min) and concentrated to a volume of approximately 155 ml by using an ultrafiltration cell (Amicon Co., Beverly, Mass.) equipped with a PM 10 membrane. The buffer was chanced to 50 mM sodium phosphate, pH 6.0, and then ammonium sulfate was added to a concentration of 0.8 M. The solution was centrifuged (20,000×g, 10 min) at 4° C. to remove precipitated material. More than 80% of the β-glucosidase activity was found in the supernatant which was loaded on a Phenyl Superose 10/10 (Pharmacia, Piscataway, N.J.) column equilibrated with 50 mM sodium phosphate buffer, pH 6.0, containing 0.8 M ammonium sulfate. Phenyl Superose is used in hydrophobic interaction chromatography. This resin contains phenyl groups linked to a cross-linked agarose matrix. The major β-glucosidase fraction did not bind to the column. This nonbound sample was then concentrated, and the buffer was changed to 20 mM piperazine-HCl, pH 6.0. The solution was applied to a Mono Q 5/5 (Pharmacia) strong anion exchange column equilibrated with 20 mM piperazine-HCl, pH 6.0. The enzyme bound to the column. Two peaks of activity were eluted with a linear gradient of NaCl (0 to 1 M). The major fraction was concentrated and changed into 20 mM formic acid buffer, pH 4.0. The sample was applied to a reverse phase Resource S column (Pharmacia). The enzyme did not adsorb to the column. Final purification was achieved by gel filtration over a Superdex 200 26/60 gel filtration column (Pharmacia) equilibrated with 20 mM sodium phosphate buffer, pH 6.0, containing 100 mM NaCl. Fractions containing β-glucosidase were stored at –20° C. until further analysis. Procedures for partial purification of the cell-associated β-glucosidases were generally identical to those for the secreted BglA except that cell extract rather than culture supernatant was the starting material.

Example 9

Analytical Methods

Sodium-dodecyl sulfate-polyacrylamide (7.5 and 10%) gel electrophoresis (SDS-PAGE) was carried out in Laemmli's buffer [Laemmli (1970) *Nature* (London) 227:680–685]. High-molecular-weight protein standards (Bio-Rad) were used as markers. Electrophoresis was performed in a Mini-Protein II cell and gels were stained with Coomassie brilliant blue R 250 [Fairbanks et al. (1971) *Biochemistry* 10:2606–2616]. β-Glucosidase activity bands in native gels were visualized by the method of Rutenburg et al. [Rutenburg et al. (1960) *J. Histochem. Cytochem.* 8:268–272] with 6-bromo-naphthyl-β-D-glucopyranoside as substrate.

The carbohydrate content of the purified enzyme was determined by using the phenol-sulfuric method of Dubois et al. [Dubois et al. (1956) *Analytic. Chem.* 28:350–356] with mannose as standard. Protein content was measured according to Lowry et al. [(1951) *J. Biol. Chem.* 193:265–273] with bovine serum albumin as standard.

The pH optimum was determined by performing assay with either pNPG or cellobiose as substrate at 40° C. in the following buffer systems: 0.1 M sodium acetate (pH 3.8 to 5.6), 0.1 M sodium phosphate (pH 5.8 to 7.6) and 0.1 M HEPES-NaOH (pH 8.0 to 8.6). Enzyme stability at different pH values was determined by measuring the residual activity after incubating the enzyme for 24 h at 4° C. with the buffers above plus glycine-HCl for pH 3.0 to 3.4 and piperazine-HCl for pH 9.0 to 10.2. The effect of the temperature on β-glucosidase activity was determined by assaying the enzyme at temperatures from 30 to 65° C. To assess the stability of the glycosylated and deglycosylated BglA at various temperatures, enzyme preparations was incubated in 50 mM sodium phosphate buffer, pH 6.0, from 10 min to 8 h in temperatures from 40 to 60° C. During the time course, aliquots were withdrawn and kept on ice. Remaining activity in the samples were determined under standard assay conditions.

Several α- and β-glucosides (1 mM) and polysaccharides (0.5%, wt/vol) were tested as substrates for the purified enzyme. ρ-Nitrophenol [Herr et al. (1978) *Appl. Microbiol. Biotechnol.* 5:29–36] and glucose were determined as described above. Reducing sugars were determined following the procedure of Miller [Miller (1959) *Anal. Chem.* 31:426–428].

To measure kinetic parameters, hydrolysis rates were done varying the concentrations of pNPG (0.05 to 10 mM) and cellobiose (0.05 to 1.0 mM). The inhibition by glucose was evaluated with only pNPG as substrate, while the inhibitory effect of glucono-1,5-lactone was verified with both pNPG and cellobiose as substrates. $K_m$, $V_{max}$ and $K_i$ values were obtained from Lineweaver-Burk plots.

For N-terminal sequence analysis, proteins were separated on SDS-PAGE [Laemmli et al. (1970) *Nature* (London) 227:680–685] and transferred to polyvinylidine difluoride membranes in a Mini Trans-Blot cell (Bio-Rad Laboratories). Protein bands on the membranes were visualized by Coomassie Blue R-250 staining and excised using a razor blade. N-terminal amino acid sequencing of the protein bands was performed on an Applied Biosystems model 477A gas phase sequencer equipped with an automatic on-line phenylthiohydantion analyzer.

TABLE 1

Summary of purification of recombinant Orpinomyces PC-2 BglA from the culture medium of *S. cerevisiae*.

| Purification step | Total protein (mg) | Total unit[a] (μmole/min) | Sp. act. (μmole/min/mg) | Yield (%) |
|---|---|---|---|---|
| Culture filtrate | 480.0 | 326.8 | 0.68 | 100.0 |
| Concentrated supernatant | 165.3 | 319.7 | 1.93 | 97.8 |
| Phenyl Sepharose | 17.1 | 101.4 | 5.9 | 31.0 |
| Mono Q | 5.2 | 66.0 | 12.8 | 20.2 |
| Resource S | 2.23 | 38.3 | 17.2 | 11.7 |
| Superdex 200 | 0.17 | 3.2 | 18.8 | 1.0 |

[a]Activities were measured with pNPG as substrate.

TABLE 2

Some properties of the purified recombinant BglA of Orpinomyces produced in S. cerevisiae.

| | |
|---|---|
| Molecular mass | |
| Deduced | 75,227 Da |
| Before deglycosylation | 110,000 Da |
| After N-glycosidase F treatment | 87 and 97 Da |
| Optimum pH at 40° C. | 5.5–7.5 |
| Optimum Temperature at pH 6.0 | 55° C. |
| $K_m$ | |
| pNPG | 0.762 mM |
| Cellobiose | 0.310 mM |
| $V_{max}$ | 8.20 µmole/min/mg |
| pNPG | |
| Cellobiose | 6.20 µmole/min/mg |
| $K_I$ of Glucose | 3.6 mM |

TABLE 3

Substrate specificity of the Orpinomyces BglA purified from S. cerevisiae[a] culture.

| Substrate (1 mM) | Specific activity[b] (µmole/min/mg) |
|---|---|
| p-nitrophenyl-β-glucosidase | 2.10 |
| Cellobiose (β-1,4) | 1.87 |
| o-nitrophenyl-β-glucosidase | 2.99 |
| Sophorose (β-1,2) | 4.53 |
| Laminaribiose (β-1,3) | 6.10 |

[a]Conditions were 40° C. and pH 6.0.
[b]Activity on gentiobiose (β-1,6-glucoside), methyl-β-glucoside, p-nitrophenyl-β-xyloside, salicin, maltose, sucrose, lactose, xylan (1.0%, wt/vol), Avicel (1.0%, wt/vol), or carboxymethylcellulose (1.0%, wt/vol) was less than 1.0% of that on p-nitrophenyl-β-glucoside.

TABLE 4

Activities of the cellulase preparation from T. reesei

| Type | U/ml |
|---|---|
| CMCase | 189.8 |
| Filter paper activity (FPA) | 13.6 |
| β-Glucosidase (pNPGase) | 2.0 |

TABLE 5

HPLC analysis of products of filter paper hydrolysis

| Time | Enzymes | G1 | G2 | G3 | % (G) |
|---|---|---|---|---|---|
| 1 h | T. reesei | 0.34 | 0.74 | 2.6 | 100 |
| | T. reesei + CelF | 1.0 | 1.34 | trace | 298 |
| | T. reesei + BglOr | 1.80 | trace | trace | 537 |
| | T. reesei + CelF + BglOr | 1.75 | 0.15 | trace | 522 |
| | CelF | trace | 0.016 | 0.011 | — |
| 3 h | T. reesei | 1.0 | 1.34 | trace | 100 |
| | T. reesei + CelF + BglOr | 4.36 | trace | trace | 437 |
| | CelF | trace | 0.04 | 0.021 | — |

BglOr: β-glucosidase of Orpinomyces PC-2
CelF: Cellulase F of Orpinomyces PC-2

TABLE 6

HPLC analysis of products of Avicel hydrolysis

| Enzymes | G1 | G2 | G3 | % (G) |
|---|---|---|---|---|
| T. reesei | 1.03 | 1.52 | — | 100 |
| T. reesei + CelF | 1.54 | 2.04 | — | 150 |
| T. reesei + BglOr | 7.20 | — | — | 699 |
| T. reesei + CelF + BglOr | 7.92 | — | — | 769 |
| CelF | — | 0.026 | 0.010 | — |

TABLE 7

HPLC analysis of products of CMC hydrolysis

| Time | Enzymes | G1 | G2 | G3 | G4 | G5 |
|---|---|---|---|---|---|---|
| 0.5 h | T. reesei | — | 0.14 | 0.038 | 0.019 | 0.013 |
| | T. reesei + CelF | — | 0.33 | 0.11 | 0.011 | — |
| | T. reesei + BglOr | 0.36 | 0.13 | 0.025 | 0.01 | — |
| | CelF | — | 0.15 | 0.074 | 0.009 | — |
| 2 h | T. reesei | 0.005 | 0.37 | 0.094 | 0.014 | — |
| | T.reesei + CelF | — | 0.43 | 0.11 | trace | — |
| | T. reesei + BglOr | 1.12 | 0.021 | — | — | — |
| | CelF | 0.23 | 0.095 | — | — | — |

TABLE 8

HPLC analysis of products of corn fiber hydrolysis

| Enzymes | G2 | G1 | Xyl[1] | Gal[2] | Ara[3] | % (G1) |
|---|---|---|---|---|---|---|
| T. reesei | 1.4 | 15.8 | 0.53 | 0.068 | 0.16 | 100 |
| T. reesei + BglOr | — | 22.8 | 0.57 | 0.1 | — | 144 |
| T. reesei + CelF + BglOr | 0.055 | 21.76 | 0.64 | 0.15 | — | 138 |

[1]Xyl: xylose
[2]Gal: galactose
[3]Ara: arabinose

TABLE 9

Comparison of glucose production by *T. reesei* cellulase supplemented with recombinant β-glucosidase of Orpinomyces PC-2 or *A. niger* β-glucosidase (HPLC analysis of products, Avicel as the substrate)

| Enzymes | | Products (mMol/L) | | |
|---|---|---|---|---|
| | | G1 | G2 | % (G) |
| *T. reesei* | | 1.5 | 1.6 | 100 |
| *T. reesei* | + BglOr (20 μl) | 5.2 | — | 347 |
| | + BglAn (20 μl)[1] | 4.8 | 0.30 | 320 |
| *T. reesei* | + BglOr (10 μl) | 5.1 | — | 340 |
| | + BglAn (10 μl) | 3.4 | 0.39 | 227 |
| *T. reesei* | + BglOr (5 μl) | 4.9 | 0.11 | 327 |
| | + BglAn (5 μl) | 3.0 | 0.76 | 200 |
| *T. reesei* | + BglOr (2.5 μl) | 3.5 | 0.26 | 233 |
| | + BglAn (2.5 μl) | 2.2 | 0.88 | 147 |
| *T. reesei* | + BglOr (1.25 μl) | 2.4 | 0.79 | 160 |
| | + BglAn (1.25 μl) | 1.7 | 1.0 | 113 |
| *T. reesei* | + CelF + BglOr (20 μl) | 5.9 | — | 393 |
| | + CelF + BglAn (20 μl) | 4.0 | 0.28 | 267 |
| *T. reesei* | + CelF + BglOr (10 μl) | 5.7 | — | 380 |
| | + CelF + BglAn (10 μl) | 3.7 | 0.58 | 247 |
| *T. reesei* | + CelF + BglOr (5 μl) | 5.0 | 0.16 | 333 |
| | + CelF + BglAn (5 μl) | 3.0 | 0.87 | 200 |
| *T. reesei* | + CelF + BglOr (2.5 μl) | 3.5 | 0.59 | 233 |
| | + CelF + BglAn (2.5 μl) | 2.2 | 0.98 | 147 |
| *T. reesei* | +CelF + BglOr (1.25 μ | 2.4 | 1.0 | 160 |
| | + BglAn (1.25 μl) | 1.9 | 1.3 | 127 |

[1]BglAn: β-glucosidase from *A. niger*; amounts of the two β-glucosidase activity (BglOr and BglAn) are the same in each comparison study.

TABLE 10

Comparison of glucose production by *T. reesei* cellulase supplemented with recombinant β-glucosidases of Orpinomyces PC-2 or *A. niger* (HPLC analysis of products, filter paper as the substrate)

| Time (h) | Enzymes | Products (mMol/L) | | |
|---|---|---|---|---|
| | | G1 | G2 | % (G) |
| 1 | *T. reesei* | 0.40 | 0.67 | 100 |
| | *T. reesei* + BglOr | 2.22 | 0.075 | 555 |
| | *T. reesei* + BglAn | 1.03 | 0.42 | 258 |
| | *T. reesei* + CelF + BglOr | 2.29 | 0.14 | 573 |
| | *T. reesei* + CelF + BglAn | 1.15 | 0.53 | 288 |
| 3 | *T. reesei* | 1.1 | 0.66 | 100 |
| | *T. reesei* + BglOr | 4.95 | 0.14 | 450 |
| | *T. reesei* + BglAn | 2.69 | 0.67 | 245 |
| | *T. reesei* + CelF + BglOr | 5.25 | 0.16 | 477 |
| | *T. reesei* + CelF + BglAn | 2.80 | 0.80 | 255 |

TABLE 11

Comparison of $K_m$ and $K_i$ of some β-glucosidase from various microorganisms

| Source | Cellobiose affinity ($K_m$, mM) | Glucose inhibition ($K_i$, mM) |
|---|---|---|
| Orpinomyces PC-2 [Chen et al. (1994) Appl. Environ. Microbiol. 60:64–70] | 0.25 | 8.75 |
| *T. reesei* [Chen et al. (1992) Biochem. Biophys. Acta. 1121:54–60] | 2.10 | 0.62 |
| *Aspergillus niger* [Hoh et al. (1992) Appl. Microbiol. Biotechnol. 37:590–593] | 0.89 | 3.22 |
| *Aspergillus nidulans* [Kwon et al. (1992) FEMS Microbiol. Letts. 97:149–154] | 1 | 5.48 |
| *Aureobasidium pullulans* [Saha et al. (1995) In Enzymatic Degradation of Insoluble Carbohy-drates, Eds. Saddler and Penner, M.H. ACS Symposium Serious 618, pp. 197–207] | 5.65 | 1.0 |
| *Thermotoga sp* [Ruthersmith and Daniel (1993) Biochem. Biophys. Acta. 1156:167–172] | 19 | 0.42 |
| *Sporotrichum thermophile* [Bhat et al. (1993) J. Gen. Microbiol. 139:2825–2832] | 0.83 | 0.5 |
| *Clostridium thermocellum* [Katayeva et al. (1992) Enzyme Microb. Technol. 14:407–412) | 77 | Na* |

Na*, not available.

TABLE 12

Nucleotide (cDNA) and Deduced Amino Acid Sequence for Orpinomyces PC-2 β-glucosidase (Bg1A).

```
AAATAATTAAATTAAGATATATATAATAAATAAATAAAATGAAGACTCTTACTGTTTTCT
                                         M  K  T  L  T  V  F  S  8
```

TABLE 12-continued

Nucleotide (cDNA) and Deduced Amino Acid Sequence for
Orpinomyces PC-2 β-glucosidase (BglA).

```
CTGCTTTATTAGCTGTTACTGCTGCTAAGAAGTGCATTGTTAAGAGCGATGCTGCTGTTG
  A  L  L  A  V  T  A  A  K  K  C  I  V  K  S  D  A  A  V  A    28
                           ---------------------------

CTTCTGAAGCTGAAGAAGTCACTGCTGAACTTACTGCTCCAGAAGATTCTGGTGTTGAAT
  S  E  A  E  E  V  T  A  E  L  T  A  P  E  D  S  G  V  E  S    48

CTGGTGAAGATGATGAATTATTAGATTTATCTACCATTGACTACGGAGATGATGTTGACA
  G  E  D  D  E  L  L  D  L  S  T  I  D  Y  G  D  D  V  D  M    68

TGTCTACTGTTAAGAAGCTTCCAGCTGACTTCAAATGGGGTGCTGCTACTGCTGCTTACC
  S  T  V  K  K  L  P  A  D  F  K  W  G  A  A  T  A  A  Y  Q    88

AAGTTGAAGGTGCCTGGGATGAAGAAGGTCGTGGTGAATCTGTCTGGGATCACTTCACTC
  V  E  G  A  W  D  E  E  G  R  G  E  S  V  W  D  H  F  T  H   108

ATCTTTACCCAAAGAATGTCGAATCTGGTGACAGATCCAAGGACTTCTCCACTAATGGTA
  L  Y  P  K  N  V  E  S  G  D  R  S  K  D  F  S  T  N  G  N   128

ACATTGCTTGTGATTCTTACCACAAGTTCGACGAAGATGTTAAAATGTTAAAGCTCATGA
  I  A  C  D  S  Y  H  K  F  D  E  D  V  K  M  L  K  L  M  N   148

ATGCTAAATACTACCGTTTCTCTATTTCATGGCCACGTCTTTTCCCAGATGGTCAAGCCA
  A  K  Y  Y  R  F  S  I  S  W  P  R  L  F  P  D  G  Q  A  R   168

GAAAGGTTGACGGTAAATGGAACGTCAATGAAAAGGGTGCTGAATACTACGATATGGTTA
  K  V  D  G  K  W  N  V  N  E  K  G  A  E  Y  Y  D  M  V  I   188

TCAATACTCTTCTTAAAAACGATATTGTTCCATTCGTTACTCTTTACCACTGGGATCTTC
  N  T  L  L  K  N  D  I  V  P  F  V  T  L  Y  H  W  D  L  P   208

CATACGCTCTCCACGAAAAGTATGGTGGTTGGTTAGATTACCACTCCCAAGATGATTTCG
  Y  A  L  H  E  K  Y  G  G  W  L  D  Y  H  S  Q  D  D  F  A   228

CCAAATACGCCGAATTCTGTTTCGAACGTTTTGGTGACCGTGTCAAGAACTGGATTACTA
  K  Y  A  E  F  C  F  E  R  F  G  D  R  V  K  N  W  I  T  I   248

TTAACGAACCATGGGTTAACTGTGTTTCTGGTTACCGTCTTGGTCCAGGTAAGGCTCCAT
  N  E  P  W  V  N  C  V  S  G  Y  R  L  G  P  G  K  A  P  Y   268

ACAGATGTACTGGTGAAGCTCCACGTAAGCTCCAAAACTCCACCGATCTTGACTTAGAAG
  R  C  T  G  E  A  P  R  K  L  Q  N  S  T  D  L  D  L  E  G   288

GAGGTTGTTCCTACGAAATTGGTCCAACTCAATACTCTAAGAACTCTGAACCTCTTCCAG
  G  C  S  Y  E  I  G  P  T  Q  Y  S  K  N  S  E  P  L  P  A   308

CTAACCGTGTTCCACAAAAGTTAGAAGATGTCTGGTGTTCCCACAATATTCTTCTTGGTC
  N  R  V  P  Q  K  L  E  D  V  W  C  S  H  N  I  L  L  G  H   328

ACGCTAAGGCTGTTAAGGTCTACCGTGAAAAATTCCAAAAGAAGCAAAAGGGTCTTATTG
  A  K  A  V  K  V  Y  R  E  K  F  Q  K  K  Q  K  G  L  I  G   348

GTATTACCGTTGATGGTGAAGCTCAAATTCCATGGGTTGAACCAGGTATGACCAAGAAGG
  I  T  V  D  G  E  A  Q  I  P  W  V  E  P  G  M  T  K  K  E   368

AATACGAAAACAACTTAAAGTACGCCAACTTAGCTGCTGAATTCCGTATTGGTTGGTACT
  Y  E  N  N  L  K  Y  A  N  L  A  A  E  F  R  I  G  W  Y  S   388

CTGACCCACCAATGGTTGGTGACTATCCAAAGTCCGTTAAGGAAAGAATGGGTAAGGACT
  D  P  P  M  V  G  D  Y  P  K  S  V  K  E  R  M  G  K  D  L   408

TACCAGAATTCACTGAAGAAGAAAAGAAGATCTTAAAGGGATCTTCCTCTGACTTCTTAG
  P  E  F  T  E  E  E  K  K  I  L  K  G  S  S  S  D  F  L  G   428

GTTGGAACACCTACACTGCTCACTGGGCTGCTCAAGCTAAGAACGAAGATGGTTCTTACA
  W  N  T  Y  T  A  H  W  A  A  Q  A  K  N  E  D  G  S  Y  I   448

TTCAACCACCAACTGCCGAAGAAGCTAACTTCGACAACTCCAAGAAGGATATGTGGGATG
  Q  P  P  T  A  E  E  A  N  F  D  N  S  K  K  D  M  W  D  D   468

ATAACTGTAAGGGACGTGGTGATGGTTGGACTTGTATTCCACCAACTCTTGGTTCCCAAG
  N  C  K  G  R  G  D  G  W  T  C  I  P  P  T  L  G  S  Q  A   488

CTGGTTCTTCCTGGAACACTAAGTTCGCTCCAACTATCCGTGTTGGTCTTAACTGGTTCT
  G  S  S  W  N  T  K  F  A  P  T  I  R  V  G  L  N  W  F  S   508
```

TABLE 12-continued

Nucleotide (cDNA) and Deduced Amino Acid Sequence for Orpinomyces PC-2 β-glucosidase (Bg1A).

```
CCAAGCGTTACGAAGGTTTAATTAAGAACGGTATCGTTATTACTGAAAACGGTTGTGCCC
  K   R   Y   E   G   L   I   K   N   G   I   V   I   T   E   N   G   C   A   Q
528

AACCAAACTACAAGGTTGCTCGTGCTAATGATGAAGTTACTAAGAAGTACTTCGAATCTA
  P   N   Y   K   V   A   R   A   N   D   E   V   T   K   K   Y   F   E   S   I   548

TTGGTCAACCAAAGTATGCTGATACTTACAAGGAAGAAGATATTGAAAGAGAAGACAACT
  G   Q   P   K   Y   A   D   T   Y   K   E   E   D   I   E   R   E   D   N   L   568

TAGAAGGTACTCTTATGCACGATACCTACCGTATTGACTGGTACGACCAATACCTTAAGA
  E   G   T   L   M   H   D   T   Y   R   I   D   W   Y   D   Q   Y   L   K   N   588

ACCTTCGTCTTGCCTACGCCGTCGATAACATCGATGTCCGTGGTTACATGGCCTGGTCTT
  L   R   L   A   Y   A   V   D   N   I   D   V   R   G   Y   M   A   W   S   L   608

TACTTGATAACTTTGAATGGGAAAACGGTTACGAAACTCGTTTTGGTATGACTTACATTG
  L   D   N   F   E   W   E   N   G   Y   E   T   R   F   G   M   T   Y   I   D   628

ACTTCTACAATGACAAGGAAATGAAGCGTGTTCCAAAGGATTCCCTTGAACATCTTGGTC
  F   Y   N   D   K   E   M   K   R   V   P   K   D   S   L   E   H   L   G   Q   648

AATGGTACCTCGAAAATGTTGAACAAAACTAAATTTCTTAAAAATTTATAATAATATTTT
  W   Y   L   E   N   V   E   Q   N   *                                           657

ATTACAATTATAAATAAATATATTAATAATGGAATTATTTTATTCACTTCTTTTGCTATA

AGTAGTGAAATAAATTAATTTTATAATTATATAAATTTATAGAATAAATCTTTTTTGAAT

CATTAAAAATTAAAATAAATAATATACAAATTTTAATGAATAATAATGATTATTATTAAAT

ATTCTAAAGAAGATTTATAATTTTTAAGAATAAATATAAAGCAAGAAAACAAATATAATT

AAAAAAAATAAAAATTAAATATAAAATAAAAATAAAATAATAAAGCTTTGTGTTTAAAAT

AAAATAGAGTAGTAAAAGCTATTCGCTATTCTTAATAAATATAAAAATATAAAATAAAGT

TAAAAATTTAAATAAAATAAAAAATATTAATAAAA
```

TABLE 13

Comparison of β-Glucosidase Sequences from Orpinomyces PC-2 (Orpin), *Cavia porcellus* (Capor), *Bacillus circulans* (Bacci), *Costus speciosus* (Cosspe), *Thermoanaerobacter* (Theran), *Clostridium thermocellum* (Clotm) and *Thermotoga maritima* (Thema).

```
Bgla_Orpin   65 DVDMSTVKKLPADFKWGAATAAYGVEGAWDEEGRGESVWD HFTHLYPKNVESGDRSKDFSTNGNIACDSYHKEDEDVKILKLINAKYRF
Bgl_Capor     1 .......MAFPADLVGGLPTAATQVEGQWDADGRGPCVWD TPTHQGGERVFKNQ.......TGDVACGSYTLWEEDLKCIKQIGLTHYRF
Bgl_Cosspe   87 SKVQLGRSSFPRGFIFGAASAAYQVEGAWNEGGRGPSIWD TPTHDHPEKIADHS.......NGDKATDSYKKYKEDVKLLKDIGLDSYRF
Bgla_Bacci    1 .....STHMFPSDFKWGVATAAYQIEGAYNEDGRGMSIWD TFAHT.PGKVKNGD.......NGNYACDSYHRVEEDVQLLKDIGVKVYRF
Bgla_Thema    1 ....MNVKKFPEGFLWGVATASYQIEGSPLADGAGMSIWH TPSHT.PGNVKNGD.......TGDYACDHYNRWKEDIEIIEKLGVKAYRF
Bgla_Clotm    1 ...MSKIT.FPKDFIWGSATAAYQIEGAYNEDGKGESIWD RFSHT.PGNIADGH.......TGDYACDHYRYEEDIKIMKEIGIKSYRF
Bgl_Theran    1 ...MIKLAKFPRDFVWGTATSSYQIEGAVNEDGRTPSIWD TFSKT.EGKTYKGH.......TGDVACDHYHRYKEDVEIIKFIGVKAYRF Bgla_Orpin  155 SISWPRLFPDGQARKVDGKWNVNEKGAEYYDMVINTLLKKNDIVPFVTLYHWDLPYALHEKYGGWLLYHQDDPAKYAEFCFFRFGDRVKN
Bgl_Capor    77 SISWSRLLPDGT.TG.....FINQKGVDYYNKLIDDLLTNGVTPVVTLYHFDLPQ.ALSDQGGWLSEAIIIVPDKYAQFCFSTFGNRVRQ
Bgl_Cosspe  170 SISWSRTLPKGTLQG.....GINQEGIQYYNDLINELLKKNGIRPMVTLFHWDVPQALEQSYKGFRSSEIVNDPKDYAQICFKEFGDRVKH
Bgla_Bacci   78 SISWPRVLPQGT..G.....EVNRAGLDYYHRLVDELLANGIEPFCTLYHWDLPQ.ALQDQGGWGSRIIIDAFAEYAELMFKELGGKIKQ
Bgla_Thema   79 SISWPRILPEGT..G.....RVNQKGLDFYNRLIDTLLEKGITPFVTIYHWDLP.FALQLKGGWANREIADWFAEYSRVLFENFGDRVKN
Bgla_Clotm   79 SISWPRIFPEGT..G.....KLNQKGLDFYKRLTNLLLENGIMPAITLYHWDLPQKLQQK.GGWKNRDITDYFTEYSEVIFKNLEDIVPI
Bgla_Theran  80 SIAWPRIFPEE...G.....KYNPKGMDFYKKLIDELQKRDIVFAATIYHWDLPQWAYQKGGGWLNRESIKWYVEYATKLFFELGDATPL Bgla_Orpin  245 WITINEPWVNCYSGYRLGPGKAPYRCTGEAPRKLQNSTDLDLEGGCEYEIGPTQYSKNSEPLPANRVPQKLEDVWCSHNILLGHAKAVKV
Bgl_Capor   160 WITINEPNVLCAMGYDLGF.......FAPGVSQL......GTGGYQA........................AHNMIKAHARAWHS
Bgl_Cosspe  255 WITLNEPWSLSTMGYAFGR.......HAPGRCSTWYGCPAGDSANEPYEV....................THNLLAHANAVKI
Bgla_Bacci  160 WITFNEPWCMAFLSNYLGV.......HAPGNKDLG..........LAIDV........................SHHLSVAHGRAVTL
Bgla_Thema  161 WITLNEPWVVAIVGHLYGV.......HAPGMRDIY..........VAFRA........................VHNLRAHARAVKY
Bgla_Clotm  161 WFTHNEPGYVSLLGHFLGI.......HAPGIKDLR..........TSLEV........................SHNLLSHGKAVKL
Bgl_Theran  162 WITHNEPWCSSILSYGIGE.......HAPGHKNYR..........EALIA........................AHHILLSHGEAVKA
```

TABLE 13-continued

Comparison of β-Glucosidase Sequences from Orpinomyces PC-2 (Orpin),
*Cavia porcellus* (Capor), *Bacillus circulans* (Bacci), *Costus speciosus* (Cosspe),
Thermoanaerobacter (Theran), *Clostridium thermocellum* (Clotm) and
*Thermotoga maritima* (Thema).

```
Bgla_Orpin 335 YREKPQKKQKGLIGITPDGEAQIPKVEPGMTKKEYNNLKYANLAAEF.RIGWYSDPPMM.GDYPKSVKERMGKDLPK..........PT
Bgl_Capor  208 YDSLFREKQKGMVSLSDF....CIRPQPENPNS..VLDQKAAERAINF.QFDFFAKPIFIDKDYPELVKSQIASMSEKQGYPSSRLSKPT
Bgl_Cosspe 312 YRDNYKATQNGEIGILLN....SLRYPP.YSKS..HEDVEAATRALDFM.FGWYMDPLV.NGDYPFIMRALVRD...RLPF.......PT
Bgla_Bacci 207 FRE..LGI.SGEIGIAPN....TSWAVP.YRRT..KEDMEACLRVNGWSG.DWYLDPIY.FGEYPKFMLDWYENLGYKPPI.......V.
Bgla_Thema 208 FRE...TVKDGKIGIVFN...NGYFPP.ASEK..EEDIRAVRFMHQFNNYPLFLNPIY.RGDYPELVLPAREYLPE..........NY
Bgla_Clotm 208 FRE..MNI.DAQIGIALN....LSYHYP.ASEK..AEDIEAAELSFSLAG.RNYLDPVL.KGRYPENALKLYKKKGIPLSF........P
Bgl_Theran 209 YRE..MNIKGSKIGILLN....LTPAYP.ASEK..EEDKLAAQYADGFAN.RWELDPIF.KGNYPEDMMSLYSKIIGPFDF......IK Bgla_Orpin 413 EEKKILKSSSDPLGWNTYTAHWAAQAKNEDGSYIQPPTAEEANFDNSKKDMWDDNCKGRGDGWTCTPPTLGSQAGSSWNTKYAPTIRV
Bgl_Capor  291 EEKKMIKG.TADRFAVQYYTRFIRHKENKEAELGILQDAEIELPSDPSWK........GVGWVR..............VVPWGIRK
Bgl_Cosspe 383 HAKSELIKG.SYDFIGINYYSNYAQHAPVTEDHTPDNSYFDSYVNQSGEKN.........GVPIGPLQ........GSWIYFYPRGLKE
Bgla_Bacci 277 QGDMELIHQ.PIDFIGINYYSSMNRYNPGFAGGMLS....SEAISMGAPKT........DIGWE...............IYAEGLYD
Bgla_Thema 277 KDDMSEIQE.KIDFYGLNYYSGHLVKFDP...DAPAK....VSFVERDLPKT.........AMGWE...............IVPEGIYW
Bgla_Clotm 278 EDDLKLISQ.PIDRIAFNNYSSEFIKYDPSSESGFSP....ANSILEKFEKT.........DMGWI...............IVPEGLYD
Bgl_Theran 281 EGDLETISV.PIDFLGVNYYTRSIVKYD...EDSMLK....AENVPGPGKRT........EMGWE................ISPEHLYD Bgla_Orpin 503 GLNWFSKRYEGLIKNGIVITENGCAQPNYKVARANDEVTKKYFESIGQPKYADTYKEEDIERALNLEGTLMHDPYRIDWYDQYLKMLRLA
Bgl_Capor  356 LINYIKDTYN...NPVIYITENGFPQ....................DDPPS....IDDTQRWECTRQTFEELFKA
Bgl_Cosspe 455 LLLYVKRRYC...NPKIYITENGTA.........................EVEKEKGVPLHDPERKEYLTYHLAQVLQA
Bgla_Bacci 337 LLRYTADKYG...NPTLYITENGACY.............................NDGLSLDGRIHDQRRIDYLAMHLIOASRA
Bgla_Thema 334 ILKKVKEEYN...PPEVYITENGAAF.............................DDVVSRDGRVHDQNRIDYLKAHIGQAWKA
Bgla_Clotm 338 LLMLLDRDYG...KPNIVISENGAAF.................................KDEIGSNGKIEDKRIQYLKDYLTQAQRA
Bgl_Theran 338 LLKRLDREYT...KLPMYITENGAAF.................................KDEVTRDGRVHDDERIEYIKEHLKAAAKF Bgla_Orpin 593 YAVDNIDVRGYMAWSLLDNFEWENGYETRFGNTYIDFYNDKEMKRVPKDSLEHLGQWYLENVEON*.   SEQUENCE ID NO:2
Bgl_Capor  404 IHVDKVNLQLYCAWSLLDNFEWNDGYSKRFGLFHVD.FEDPAKPRVPVTSAKEYAKIIRNNGLERPQ   SEQUENCE ID NO:8
Bgl_Cosspe 506 IR.EGVRVKGHFTWALTDNFEWDKGYTERFGLIYID.YDKDFN.RQPKDSTKWFSKFLRT.......   SEQUENCE ID NO:9
Bgla_Bacci 389 IE.DGINLKGYMEWSLMDNFEWAEGYGMRFGLVHVD.YD.TLM.RTPRDSFYWYKGVISRGWLDL..   SEQUENCE ID NO:10
Bgla_Thema 386 IQ.EGVPLKGYFVWSLLDNFEWAEGYSKRPGIVYYD.YS.TQK.RLVKDSGYWYSNVVKNNGLED..   SEQUENCE ID NO:11
Bgla_Clotm 390 IQ.EGVNDKAYYLWSLLDNFEWAYGYNKRPGIVHVN.FD.TLE.RKIKDSGYWYKEVIKNNGF....   SEQUENCE ID NO:12
Bgl_Theran 390 IG.EGGNIKGYFVWSLMDNFEWAHGYSKRPGIVYYD.YT.TQK.RILKDSALWYKEVILDDGIED..   SEQUENCE ID NO:13
```

What is claimed is:

1. A non-naturally occurring recombinant DNA molecule comprising a nucleotide sequence encoding a fungal β-glucosidase, wherein said encoded fungal β-glucosidase has an amino acid sequence as given in SEQ ID NO:2 from amino acid 1 through amino acid 641, from amino acid −16 through amino acid 641, from amino acid 24 through 641, or from amino acid 33 through 641, or a functionally equivalent sequence with at least 75% identity to one of the foregoing sequences.

2. The non-naturally occurring recombinant DNA molecule of claim 1 wherein said β-glucosidase molecule has an amino acid sequence as given in SEQ ID NO:2, from amino acid 1 through amino acid 641, from amino acid −16 through amino acid 641, from amino acid 24 through 641, or from amino acid 33 through 641.

3. The non-naturally occurring recombinant DNA molecule of claim 1 wherein said β-glucosidase molecule has an amino acid sequence as given in SEQ ID NO:2, from amino acid 1 through amino acid 641.

4. The recombinant DNA molecule of claim 1 wherein said β-glucosidase is encoded by the nucleotide sequence as given in SEQ ID NO:1 from nucleotide 156 to 2009, from nucleotide 183 to 2009, from nucleotide 87 through nucleotide 2009, or from nucleotide 39 through nucleotide 2009, or a functionally equivalent sequence with at least 75% identity to one of the foregoing sequences.

5. The recombinant DNA molecule of claim 2 wherein said β-glucosidase is encoded by the nucleotide sequence as given in SEQ ID NO:1 from nucleotide 156 to 2009, from nucleotide 183 to 2009, from nucleotide 87 through nucleotide 2009, or from nucleotide 39 through nucleotide 2009.

6. The recombinant DNA molecule of claim 1 wherein the β-glucosidase nucleotide sequence is as given in SEQ ID NO:1 nucleotides 87–2009, 156–2009 or 183–2009, or a sequence having at least 70% nucleotide sequence homology thereto and encoding a functional β-glucosidase and additionally comprises DNA encoding a signal peptide immediately up stream of and operably linked to the nucleotide sequence encoding the mature β-glucosidase protein.

7. The recombinant DNA molecule of claim 6 wherein said signal peptide has an amino acid sequence as given in SEQ ID NO:2, amino acids −16 to −1.

8. The non-naturally occurring recombinant DNA molecule of claim 6 wherein said nucleotide sequence encoding said β-glucosidase is as given in SEQ ID NO:1, nucleotides 39–2009, nucleotides 87–2009, nucleotides 156–2009, or nucleotides 183–2009.

9. A host cell comprising the recombinant DNA molecule of claim 1, wherein said host cell is a member of a species selected from the group consisting of *Escherichia coli, Saccharomyces cerevisiae*, Aspergillus, Penicillium, *Trichoderma reesei*, Pichia, Aureobasidium, Streptomyces and Bacillus.

10. A method of using the recombinant DNA molecule of claim 1 to produce a β-glucosidase in a host cell other than Orpinomyces sp. strain PC-2, said method comprising the steps of:

a) infecting or transforming said host cell capable of expressing a β-glucosidase coding region with a vector comprising a promoter active in said host cell wherein said promoter is operably linked to the coding region for said β-glucosidase as recited in claim 1; and b) culturing the infected or transformed host cell under conditions suitable for expression of said β-glucosidase coding sequence.

11. The method of claim 10 wherein said host cell is one of *Escherichia coli, Saccharomyces cerevisiae*, Aspergillus, Penicillium, *Trichoderma reesei*, Pichia, Aureobasidium Streptomyces and Bacillus.

12. The method of claim 10 wherein said vector further comprises a nucleotide sequence encoding a signal peptide operably linked between said promoter and said coding region.

13. The method of claim 10 wherein said signal peptide has an amino acid sequence as given in SEQ ID NO:2, amino acids −16 to −1.

* * * * *

UNITED STATES PATENT AND TRADEMARK OFFICE
CERTIFICATE OF CORRECTION

PATENT NO. : 6,184,018 B1
DATED : February 2, 2001
INVENTOR(S) : Li et al.

It is certified that error appears in the above-identified patent and that said Letters Patent is hereby corrected as shown below:

Column 1,
Line 62, replace "Fanuti" with -- Fanutti --.

Column 2,
Line 17, replace "thereof" with -- thereof. --.

Column 4,
Line 62, replace "(1 996)" with -- (1996) --.
Line 63, replace "(1 996)" with -- (1996) --.

Column 5,
Line 34, replace "using $^4$-methylumbelliferyl-β-D-glucoside" with
-- using 4-methylumbelliferyl-β-D-glucoside --.

Column 17,
Line 16, replace "chanced" with -- changed --.

Column 18,
Line 50, replace "phenylthiohydantion" with -- phenylthiohydantoin --.

Column 19,
Line 1, replace Table 2 with the following:

--Table 2. Some properties of the purified recombinant BglA of *Orpinomyces* produced in *S. cerevisiae*.

| | |
|---|---|
| Molecular mass | |
|     Deduced | 75,227 Da |
|     Before deglycosylation | 110,000 Da |
|     After N-glycosidase F treatment | 87 and 97 Da |
| Optimum pH at 40°C | 5.5-7.5 |
| Optimum Temperature at pH 6.0 | 55°C |
| $K_m$ | |
|     pNPG | 0.762 mM |
|     Cellobiose | 0.310 mM |
| $V_{max}$ | |
|     pNPG | 8.20 μmole/min/mg |
| Cellobiose | 6.20 μmole/min/mg |
| $K_i$ of Glucose | 3.6 mM-- |

UNITED STATES PATENT AND TRADEMARK OFFICE
CERTIFICATE OF CORRECTION

PATENT NO. : 6,184,018 B1
DATED : February 2, 2001
INVENTOR(S) : Li et al.

It is certified that error appears in the above-identified patent and that said Letters Patent is hereby corrected as shown below:

<u>Columns 25-28,</u>
Replace Table 13 with the following:

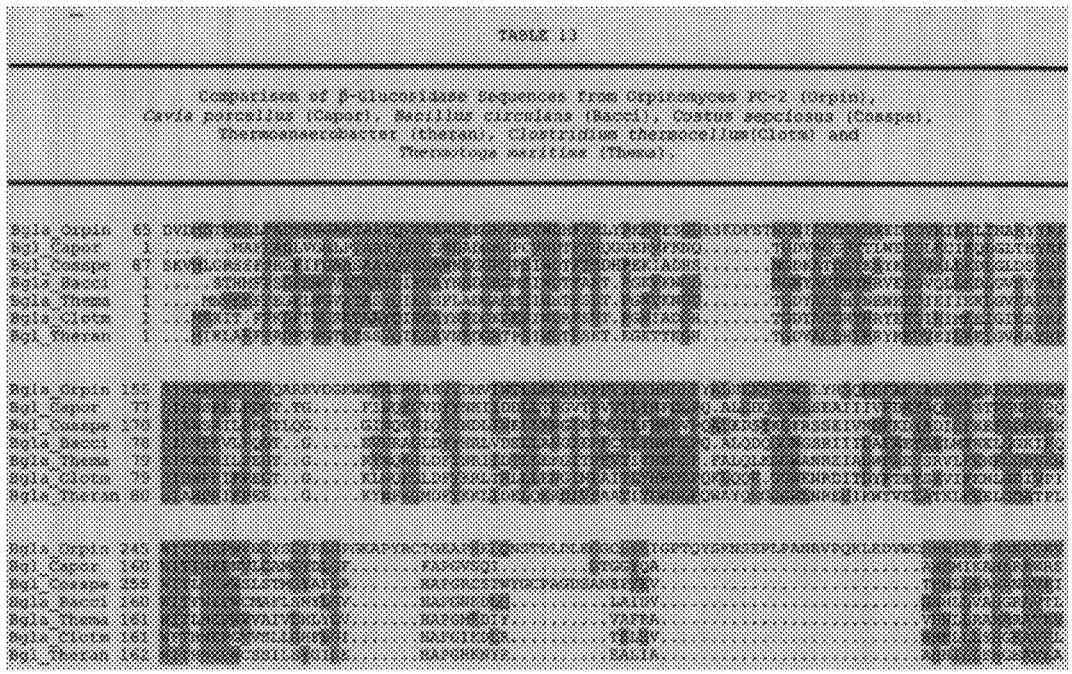

UNITED STATES PATENT AND TRADEMARK OFFICE
CERTIFICATE OF CORRECTION

PATENT NO. : 6,184,018 B1
DATED : February 2, 2001
INVENTOR(S) : Li et al.

It is certified that error appears in the above-identified patent and that said Letters Patent is hereby corrected as shown below:

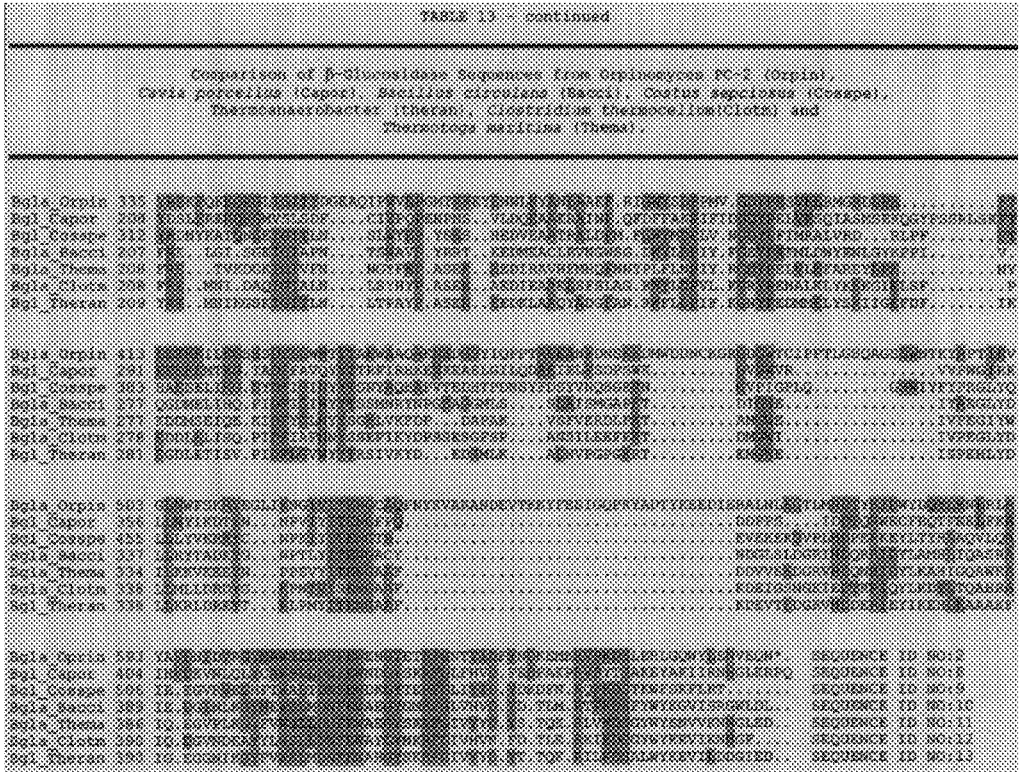

Column 54,
Line 12, replace "Aureobasidium" with -- Aureobasidium, --.

Signed and Sealed this

Seventeenth Day of December, 2002

JAMES E. ROGAN
*Director of the United States Patent and Trademark Office*

SEQUENCE LISTING

<160> NUMBER OF SEQ ID NOS: 13

<210> SEQ ID NO 1
<211> LENGTH: 2435
<212> TYPE: DNA
<213> ORGANISM: Orpinomyces sp. PC-2
<220> FEATURE:
<221> NAME/KEY: CDS
<222> LOCATION: (39)..(2009)
<220> FEATURE:
<221> NAME/KEY: mat_peptide
<222> LOCATION: (87)..(2009)

<400> SEQUENCE: 1

```
aaataattaa attaagatat atataataaa taaataaa atg aag act ctt act gtt        56
                                         Met Lys Thr Leu Thr Val
                                          -15 ttc tct gct tta tta gct gtt act gct gct aag aag tgc att gtt aag          104
Phe Ser Ala Leu Leu Ala Val Thr Ala Ala Lys Lys Cys Ile Val Lys
-10                  -5                  -1  1                5 agc gat gct gct gtt gct tct gaa gct gaa gaa gtc act gct gaa ctt          152
Ser Asp Ala Ala Val Ala Ser Glu Ala Glu Glu Val Thr Ala Glu Leu
                10                  15                  20 act gct cca gaa gat tct ggt gtt gaa tct ggt gaa gat gat gaa tta          200
Thr Ala Pro Glu Asp Ser Gly Val Glu Ser Gly Glu Asp Asp Glu Leu
            25                  30                  35 tta gat tta tct acc att gac tac gga gat gat gtt gac atg tct act          248
```

```
                                                                    -continued Leu Asp Leu Ser Thr Ile Asp Tyr Gly Asp Asp Val Asp Met Ser Thr
    40                  45                  50 gtt aag aag ctt cca gct gac ttc aaa tgg ggt gct gct act gct gct         296
Val Lys Lys Leu Pro Ala Asp Phe Lys Trp Gly Ala Ala Thr Ala Ala
 55                  60                  65                  70 tac caa gtt gaa ggt gcc tgg gat gaa gaa ggt cgt ggt gaa tct gtc         344
Tyr Gln Val Glu Gly Ala Trp Asp Glu Glu Gly Arg Gly Glu Ser Val
                 75                  80                  85 tgg gat cac ttc act cat ctt tac cca aag aat gtc gaa tct ggt gac         392
Trp Asp His Phe Thr His Leu Tyr Pro Lys Asn Val Glu Ser Gly Asp
             90                  95                 100 aga tcc aag gac ttc tcc act aat ggt aac att gct tgt gat tct tac         440
Arg Ser Lys Asp Phe Ser Thr Asn Gly Asn Ile Ala Cys Asp Ser Tyr
            105                 110                 115 cac aag ttc gac gaa gat gtt aaa atg tta aag ctc atg aat gct aaa         488
His Lys Phe Asp Glu Asp Val Lys Met Leu Lys Leu Met Asn Ala Lys
        120                 125                 130 tac tac cgt ttc tct att tca tgg cca cgt ctt ttc cca gat ggt caa         536
Tyr Tyr Arg Phe Ser Ile Ser Trp Pro Arg Leu Phe Pro Asp Gly Gln
135                 140                 145                 150 gcc aga aag gtt gac ggt aaa tgg aac gtc aat gaa aag ggt gct gaa         584
Ala Arg Lys Val Asp Gly Lys Trp Asn Val Asn Glu Lys Gly Ala Glu
                155                 160                 165 tac tac gat atg gtt atc aat act ctt ctt aaa aac gat att gtt cca         632
Tyr Tyr Asp Met Val Ile Asn Thr Leu Leu Lys Asn Asp Ile Val Pro
            170                 175                 180 ttc gtt act ctt tac cac tgg gat ctt cca tac gct ctc cac gaa aag         680
Phe Val Thr Leu Tyr His Trp Asp Leu Pro Tyr Ala Leu His Glu Lys
        185                 190                 195 tat ggt ggt tgg tta gat tac cac tcc caa gat gat ttc gcc aaa tac         728
Tyr Gly Gly Trp Leu Asp Tyr His Ser Gln Asp Asp Phe Ala Lys Tyr
200                 205                 210 gcc gaa ttc tgt ttc gaa cgt ttt ggt gac cgt gtc aag aac tgg att         776
Ala Glu Phe Cys Phe Glu Arg Phe Gly Asp Arg Val Lys Asn Trp Ile
215                 220                 225                 230 act att aac gaa cca tgg gtt aac tgt gtt tct ggt tac cgt ctt ggt         824
Thr Ile Asn Glu Pro Trp Val Asn Cys Val Ser Gly Tyr Arg Leu Gly
                235                 240                 245 cca ggt aag gct cca tac aga tgt act ggt gaa gct cca cgt aag ctc         872
Pro Gly Lys Ala Pro Tyr Arg Cys Thr Gly Glu Ala Pro Arg Lys Leu
            250                 255                 260 caa aac tcc acc gat ctt gac tta gaa gga ggt tgt tcc tac gaa att         920
Gln Asn Ser Thr Asp Leu Asp Leu Glu Gly Gly Cys Ser Tyr Glu Ile
        265                 270                 275 ggt cca act caa tac tct aag aac tct gaa cct ctt cca gct aac cgt         968
Gly Pro Thr Gln Tyr Ser Lys Asn Ser Glu Pro Leu Pro Ala Asn Arg
280                 285                 290 gtt cca caa aag tta gaa gat gtc tgg tgt tcc cac aat att ctt ctt        1016
Val Pro Gln Lys Leu Glu Asp Val Trp Cys Ser His Asn Ile Leu Leu
295                 300                 305                 310 ggt cac gct aag gct gtt aag gtc tac cgt gaa aaa ttc caa aag aag        1064
Gly His Ala Lys Ala Val Lys Val Tyr Arg Glu Lys Phe Gln Lys Lys
                315                 320                 325 caa aag ggt ctt att ggt att acc gtt gat ggt gaa gct caa att cca        1112
Gln Lys Gly Leu Ile Gly Ile Thr Val Asp Gly Glu Ala Gln Ile Pro
            330                 335                 340 tgg gtt gaa cca ggt atg acc aag aag gaa tac gaa aac aac tta aag        1160
Trp Val Glu Pro Gly Met Thr Lys Lys Glu Tyr Glu Asn Asn Leu Lys
        345                 350                 355
```

-continued

```
tac gcc aac tta gct gct gaa ttc cgt att ggt tgg tac tct gac cca    1208
Tyr Ala Asn Leu Ala Ala Glu Phe Arg Ile Gly Trp Tyr Ser Asp Pro
360                 365                 370 cca atg gtt ggt gac tat cca aag tcc gtt aag gaa aga atg ggt aag    1256
Pro Met Val Gly Asp Tyr Pro Lys Ser Val Lys Glu Arg Met Gly Lys
375                 380                 385                 390 gac tta cca gaa ttc act gaa gaa gaa aag aag atc tta aag gga tct    1304
Asp Leu Pro Glu Phe Thr Glu Glu Glu Lys Lys Ile Leu Lys Gly Ser
                395                 400                 405 tcc tct gac ttc tta ggt tgg aac acc tac act gct cac tgg gct gct    1352
Ser Ser Asp Phe Leu Gly Trp Asn Thr Tyr Thr Ala His Trp Ala Ala
        410                 415                 420 caa gct aag aac gaa gat ggt tct tac att caa cca cca act gcc gaa    1400
Gln Ala Lys Asn Glu Asp Gly Ser Tyr Ile Gln Pro Pro Thr Ala Glu
425                 430                 435 gaa gct aac ttc gac aac tcc aag aag gat atg tgg gat gat aac tgt    1448
Glu Ala Asn Phe Asp Asn Ser Lys Lys Asp Met Trp Asp Asp Asn Cys
440                 445                 450 aag gga cgt ggt gat ggt tgg act tgt att cca cca act ctt ggt tcc    1496
Lys Gly Arg Gly Asp Gly Trp Thr Cys Ile Pro Pro Thr Leu Gly Ser
455                 460                 465                 470 caa gct ggt tct tcc tgg aac act aag ttc gct cca act atc cgt gtt    1544
Gln Ala Gly Ser Ser Trp Asn Thr Lys Phe Ala Pro Thr Ile Arg Val
                475                 480                 485 ggt ctt aac tgg ttc tcc aag cgt tac gaa ggt tta att aag aac ggt    1592
Gly Leu Asn Trp Phe Ser Lys Arg Tyr Glu Gly Leu Ile Lys Asn Gly
        490                 495                 500 atc gtt att act gaa aac ggt tgt gcc caa cca aac tac aag gtt gct    1640
Ile Val Ile Thr Glu Asn Gly Cys Ala Gln Pro Asn Tyr Lys Val Ala
505                 510                 515 cgt gct aat gat gaa gtt act aag aag tac ttc gaa tct att ggt caa    1688
Arg Ala Asn Asp Glu Val Thr Lys Lys Tyr Phe Glu Ser Ile Gly Gln
520                 525                 530 cca aag tat gct gat act tac aag gaa gaa gat att gaa aga gaa gac    1736
Pro Lys Tyr Ala Asp Thr Tyr Lys Glu Glu Asp Ile Glu Arg Glu Asp
535                 540                 545                 550 aac tta gaa ggt act ctt atg cac gat acc tac cgt att gac tgg tac    1784
Asn Leu Glu Gly Thr Leu Met His Asp Thr Tyr Arg Ile Asp Trp Tyr
                555                 560                 565 gac caa tac ctt aag aac ctt cgt ctt gcc tac gcc gtc gat aac atc    1832
Asp Gln Tyr Leu Lys Asn Leu Arg Leu Ala Tyr Ala Val Asp Asn Ile
        570                 575                 580 gat gtc cgt ggt tac atg gcc tgg tct tta ctt gat aac ttt gaa tgg    1880
Asp Val Arg Gly Tyr Met Ala Trp Ser Leu Leu Asp Asn Phe Glu Trp
585                 590                 595 gaa aac ggt tac gaa act cgt ttt ggt atg act tac att gac ttc tac    1928
Glu Asn Gly Tyr Glu Thr Arg Phe Gly Met Thr Tyr Ile Asp Phe Tyr
600                 605                 610 aat gac aag gaa atg aag cgt gtt cca aag gat tcc ctt gaa cat ctt    1976
Asn Asp Lys Glu Met Lys Arg Val Pro Lys Asp Ser Leu Glu His Leu
615                 620                 625                 630 ggt caa tgg tac ctc gaa aat gtt gaa caa aac taaatttctt aaaaatttat  2029
Gly Gln Trp Tyr Leu Glu Asn Val Glu Gln Asn
                635                 640 aataatattt tattcaatt ataaataat atattaataa tggaattatt ttattcactt    2089
cttttgctat aagtagtgaa ataaattaat tttataatta tataaattta tagaataaat  2149
cttttttgaa tcattaaaat taaaatataat aatatacaaa ttttaatgaa taataatgat  2209
tattattaaa tattctaaag aagatttata attttaaga ataaatataa agcaagaaaa   2269
```

-continued

```
caaatataat taaaaaaaat aaaaattaaa tataaaataa aaataaaata ataaagcttt      2329
gtgtttaaaa taaaatagag tagtaaaagc tattcgctat tcttaataaa tataaaaata      2389
taaaataaag ttaaaaattt aaataaaata aaaaatatta ataaaa                    2435
```

<210> SEQ ID NO 2
<211> LENGTH: 657
<212> TYPE: PRT
<213> ORGANISM: Orpinomyces sp. PC-2

<400> SEQUENCE: 2

```
Met Lys Thr Leu Thr Val Phe Ser Ala Leu Leu Ala Val Thr Ala Ala
    -15              -10                  -5                  -1

Lys Lys Cys Ile Val Lys Ser Asp Ala Ala Val Ala Ser Glu Ala Glu
  1               5                  10                  15

Glu Val Thr Ala Glu Leu Thr Ala Pro Glu Asp Ser Gly Val Glu Ser
             20                  25                  30

Gly Glu Asp Asp Glu Leu Leu Asp Leu Ser Thr Ile Asp Tyr Gly Asp
         35                  40                  45

Asp Val Asp Met Ser Thr Val Lys Lys Leu Pro Ala Asp Phe Lys Trp
 50                  55                  60

Gly Ala Ala Thr Ala Ala Tyr Gln Val Glu Gly Ala Trp Asp Glu Glu
 65                  70                  75                  80

Gly Arg Gly Glu Ser Val Trp Asp His Phe Thr His Leu Tyr Pro Lys
             85                  90                  95

Asn Val Glu Ser Gly Asp Arg Ser Lys Asp Phe Ser Thr Asn Gly Asn
            100                 105                 110

Ile Ala Cys Asp Ser Tyr His Lys Phe Asp Glu Asp Val Lys Met Leu
        115                 120                 125

Lys Leu Met Asn Ala Lys Tyr Tyr Arg Phe Ser Ile Ser Trp Pro Arg
130                 135                 140

Leu Phe Pro Asp Gly Gln Ala Arg Lys Val Asp Gly Lys Trp Asn Val
145                 150                 155                 160

Asn Glu Lys Gly Ala Glu Tyr Tyr Asp Met Val Ile Asn Thr Leu Leu
                165                 170                 175

Lys Asn Asp Ile Val Pro Phe Val Thr Leu Tyr His Trp Asp Leu Pro
            180                 185                 190

Tyr Ala Leu His Glu Lys Tyr Gly Gly Trp Leu Asp Tyr His Ser Gln
        195                 200                 205

Asp Asp Phe Ala Lys Tyr Ala Glu Phe Cys Phe Glu Arg Phe Gly Asp
    210                 215                 220

Arg Val Lys Asn Trp Ile Thr Ile Asn Glu Pro Trp Val Asn Cys Val
225                 230                 235                 240

Ser Gly Tyr Arg Leu Gly Pro Gly Lys Ala Pro Tyr Arg Cys Thr Gly
                245                 250                 255

Glu Ala Pro Arg Lys Leu Gln Asn Ser Thr Asp Leu Asp Leu Glu Gly
            260                 265                 270

Gly Cys Ser Tyr Glu Ile Gly Pro Thr Gln Tyr Ser Lys Asn Ser Glu
        275                 280                 285

Pro Leu Pro Ala Asn Arg Val Pro Gln Leu Glu Asp Val Trp Cys
    290                 295                 300

Ser His Asn Ile Leu Leu Gly His Ala Lys Ala Val Lys Val Tyr Arg
305                 310                 315                 320

Glu Lys Phe Gln Lys Lys Gln Lys Gly Leu Ile Gly Ile Thr Val Asp
```

325                 330                 335
Gly Glu Ala Gln Ile Pro Trp Val Glu Pro Gly Met Thr Lys Lys Glu
                340                 345                 350

Tyr Glu Asn Asn Leu Lys Tyr Ala Asn Leu Ala Ala Glu Phe Arg Ile
            355                 360                 365

Gly Trp Tyr Ser Asp Pro Pro Met Val Gly Asp Tyr Pro Lys Ser Val
        370                 375                 380

Lys Glu Arg Met Gly Lys Asp Leu Pro Glu Phe Thr Glu Glu Lys
385                 390                 395                 400

Lys Ile Leu Lys Gly Ser Ser Asp Phe Leu Gly Trp Asn Thr Tyr
                405                 410                 415

Thr Ala His Trp Ala Ala Gln Ala Lys Asn Glu Asp Gly Ser Tyr Ile
            420                 425                 430

Gln Pro Pro Thr Ala Glu Ala Asn Phe Asp Asn Ser Lys Lys Asp
        435                 440                 445

Met Trp Asp Asp Asn Cys Lys Gly Arg Gly Asp Gly Trp Thr Cys Ile
    450                 455                 460

Pro Pro Thr Leu Gly Ser Gln Ala Gly Ser Ser Trp Asn Thr Lys Phe
465                 470                 475                 480

Ala Pro Thr Ile Arg Val Gly Leu Asn Trp Phe Ser Lys Arg Tyr Glu
                485                 490                 495

Gly Leu Ile Lys Asn Gly Ile Val Ile Thr Glu Asn Gly Cys Ala Gln
            500                 505                 510

Pro Asn Tyr Lys Val Ala Arg Ala Asn Asp Glu Val Thr Lys Lys Tyr
        515                 520                 525

Phe Glu Ser Ile Gly Gln Pro Lys Tyr Ala Asp Thr Tyr Lys Glu Glu
    530                 535                 540

Asp Ile Glu Arg Glu Asp Asn Leu Glu Gly Thr Leu Met His Asp Thr
545                 550                 555                 560

Tyr Arg Ile Asp Trp Tyr Asp Gln Tyr Leu Lys Asn Leu Arg Leu Ala
                565                 570                 575

Tyr Ala Val Asp Asn Ile Asp Val Arg Gly Tyr Met Ala Trp Ser Leu
            580                 585                 590

Leu Asp Asn Phe Glu Trp Glu Asn Gly Tyr Glu Thr Arg Phe Gly Met
        595                 600                 605

Thr Tyr Ile Asp Phe Tyr Asn Asp Lys Glu Met Lys Arg Val Pro Lys
    610                 615                 620

Asp Ser Leu Glu His Leu Gly Gln Trp Tyr Leu Glu Asn Val Glu Gln
625                 630                 635                 640

Asn

<210> SEQ ID NO 3
<211> LENGTH: 10
<212> TYPE: PRT
<213> ORGANISM: Orpinomyces sp. PC-2

<400> SEQUENCE: 3

Lys Lys Cys Ile Val Lys Ser Asp Ala Ala
  1               5                  10

<210> SEQ ID NO 4
<211> LENGTH: 9
<212> TYPE: PRT
<213> ORGANISM: Orpinomyces sp. PC-2

<400> SEQUENCE: 4

```
Ala Pro Glu Asp Ser Gly Val Glu Ser
 1               5
```

<210> SEQ ID NO 5
<211> LENGTH: 10
<212> TYPE: PRT
<213> ORGANISM: Orpinomyces sp. PC-2

<400> SEQUENCE: 5

```
Gly Glu Asp Asp Glu Leu Leu Asp Leu Ser
 1               5                  10
```

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gccgagctcg atgaagactc ttactgtttt c          31

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gctctagagt tagttttgtt caacattttc           30

<210> SEQ ID NO 8
<211> LENGTH: 469
<212> TYPE: PRT
<213> ORGANISM: Cavia porcellus

<400> SEQUENCE: 8

```
Met Ala Phe Pro Ala Asp Leu Val Gly Gly Leu Pro Thr Ala Ala Tyr
 1               5                  10                  15

Gln Val Glu Gly Gly Trp Asp Ala Asp Gly Arg Gly Pro Cys Val Trp
                20                  25                  30

Asp Thr Phe Thr His Gln Gly Gly Glu Arg Val Phe Lys Asn Gln Thr
            35                  40                  45

Gly Asp Val Ala Cys Gly Ser Tyr Thr Leu Trp Glu Glu Asp Leu Lys
        50                  55                  60

Cys Ile Lys Gln Leu Gly Leu Thr His Tyr Arg Phe Ser Ile Ser Trp
 65                  70                  75                  80

Ser Arg Leu Leu Pro Asp Gly Thr Thr Gly Phe Ile Asn Gln Lys Gly
                85                  90                  95

Val Asp Tyr Tyr Asn Lys Ile Ile Asp Asp Leu Leu Thr Asn Gly Val
                100                 105                 110

Thr Pro Val Val Thr Leu Tyr His Phe Asp Leu Pro Gln Ala Leu Glu
            115                 120                 125

Asp Gln Gly Gly Trp Leu Ser Glu Ala Ile Ile Glu Val Phe Asp Lys
        130                 135                 140

Tyr Ala Gln Phe Cys Phe Ser Thr Phe Gly Asn Arg Val Arg Gln Trp
145                 150                 155                 160
```

-continued

```
Ile Thr Ile Asn Glu Pro Asn Val Leu Cys Ala Met Gly Tyr Asp Leu
            165                 170                 175
Gly Phe Phe Ala Pro Gly Val Ser Gln Ile Gly Thr Gly Gly Tyr Gln
        180                 185                 190
Ala Ala His Asn Met Ile Lys Ala His Ala Arg Ala Trp His Ser Tyr
    195                 200                 205
Asp Ser Leu Phe Arg Glu Lys Gln Lys Gly Met Val Ser Leu Ser Leu
210                 215                 220
Phe Cys Ile Trp Pro Gln Pro Glu Asn Pro Asn Ser Val Leu Asp Gln
225                 230                 235                 240
Lys Ala Ala Glu Arg Ala Ile Asn Phe Gln Phe Asp Phe Ala Lys
                245                 250                 255
Pro Ile Phe Ile Asp Gly Asp Tyr Pro Glu Leu Val Lys Ser Gln Ile
            260                 265                 270
Ala Ser Met Ser Glu Lys Gln Gly Tyr Pro Ser Ser Arg Leu Ser Lys
        275                 280                 285
Phe Thr Glu Glu Lys Lys Met Thr Lys Gly Thr Ala Asp Phe Phe
    290                 295                 300
Ala Val Gln Tyr Tyr Thr Thr Arg Phe Ile Arg His Lys Glu Asn Lys
305                 310                 315                 320
Glu Ala Glu Leu Gly Ile Leu Gln Asp Ala Glu Ile Glu Leu Phe Ser
                325                 330                 335
Asp Pro Ser Trp Lys Gly Val Gly Trp Val Arg Val Pro Trp Gly
            340                 345                 350
Ile Arg Lys Leu Leu Asn Tyr Ile Lys Asp Thr Tyr Asn Asn Pro Val
        355                 360                 365
Ile Tyr Ile Thr Glu Asn Gly Phe Pro Gln Asp Asp Pro Pro Ser Ile
    370                 375                 380
Asp Asp Thr Gln Arg Trp Glu Cys Phe Arg Gln Thr Phe Glu Glu Leu
385                 390                 395                 400
Phe Lys Ala Ile His Val Asp Lys Val Asn Leu Gln Leu Tyr Cys Ala
                405                 410                 415
Trp Ser Leu Leu Asp Asn Phe Glu Trp Asn Asp Gly Tyr Ser Lys Arg
            420                 425                 430
Phe Gly Leu Phe His Val Asp Phe Glu Asp Pro Ala Lys Pro Arg Val
        435                 440                 445
Pro Tyr Thr Ser Ala Lys Glu Tyr Ala Lys Ile Ile Arg Asn Asn Gly
    450                 455                 460
Leu Glu Arg Pro Gln
465
```

<210> SEQ ID NO 9
<211> LENGTH: 476
<212> TYPE: PRT
<213> ORGANISM: Costus speciosus

<400> SEQUENCE: 9

```
Ser Lys Val Val Leu Gly Arg Ser Ser Phe Pro Arg Gly Phe Ile Phe
  1               5                  10                  15
Gly Ala Ala Ser Ala Ala Tyr Gln Val Glu Gly Ala Trp Asn Glu Gly
                 20                  25                  30
Gly Arg Gly Pro Ser Ile Trp Asp Thr Phe Thr His Asp His Pro Glu
             35                  40                  45
Lys Ile Ala Asp His Ser Asn Gly Asp Lys Ala Thr Asp Ser Tyr Lys
         50                  55                  60
```

```
Lys Tyr Lys Glu Asp Val Lys Leu Leu Lys Asp Leu Gly Leu Asp Ser
 65                  70                  75                  80

Tyr Arg Phe Ser Ile Ser Trp Ser Arg Ile Leu Pro Lys Gly Thr Leu
                 85                  90                  95

Gln Gly Gly Ile Asn Gln Glu Gly Ile Gln Tyr Tyr Asn Asp Leu Ile
                100                 105                 110

Asn Glu Leu Leu Lys Asn Gly Ile Arg Pro Met Val Thr Leu Phe His
            115                 120                 125

Trp Asp Val Pro Gln Ala Leu Glu Asp Ser Tyr Lys Gly Phe Arg Ser
        130                 135                 140

Ser Glu Ile Val Asn Asp Phe Lys Asp Tyr Ala Asp Ile Cys Phe Lys
145                 150                 155                 160

Glu Phe Gly Asp Arg Val Lys His Trp Ile Thr Leu Asn Glu Pro Trp
                165                 170                 175

Ser Leu Ser Thr Met Gly Tyr Ala Phe Gly Arg His Ala Pro Gly Arg
                180                 185                 190

Cys Ser Thr Trp Tyr Gly Cys Pro Ala Gly Asp Ser Ala Asn Glu Pro
                195                 200                 205

Tyr Glu Val Thr His Asn Leu Leu Ala His Ala Asn Ala Val Lys
        210                 215                 220

Ile Tyr Arg Asp Asn Tyr Lys Ala Thr Gln Asn Gly Glu Ile Gly Ile
225                 230                 235                 240

Thr Leu Asn Ser Leu Trp Tyr Glu Pro Tyr Ser Lys Ser His Glu Asp
                245                 250                 255

Val Glu Ala Ala Thr Arg Ala Leu Asp Phe Met Phe Gly Trp Tyr Met
                260                 265                 270

Asp Pro Leu Val Asn Gly Asp Tyr Pro Phe Ile Met Arg Ala Leu Val
        275                 280                 285

Arg Asp Arg Leu Pro Phe Phe Thr His Ala Glu Ser Glu Leu Ile Lys
    290                 295                 300

Gly Ser Tyr Asp Phe Ile Gly Ile Asn Tyr Tyr Thr Ser Asn Tyr Ala
305                 310                 315                 320

Gln His Ala Pro Val Thr Glu Asp His Thr Pro Asp Asn Ser Tyr Phe
                325                 330                 335

Asp Ser Tyr Val Asn Gln Ser Gly Glu Lys Asn Gly Val Pro Ile Gly
                340                 345                 350

Pro Leu Gln Gly Ser Trp Ile Tyr Phe Tyr Pro Arg Gly Leu Lys Glu
                355                 360                 365

Leu Leu Leu Tyr Val Lys Arg Arg Tyr Cys Asn Pro Lys Ile Tyr Ile
        370                 375                 380

Thr Glu Asn Gly Thr Ala Glu Val Glu Lys Glu Lys Gly Val Pro Leu
385                 390                 395                 400

His Asp Pro Glu Arg Lys Glu Tyr Leu Thr Tyr His Leu Ala Gln Val
                405                 410                 415

Leu Gln Ala Ile Arg Glu Gly Val Arg Val Lys Gly His Phe Thr Trp
                420                 425                 430

Ala Leu Thr Asp Asn Phe Glu Trp Asp Lys Gly Tyr Thr Glu Arg Phe
        435                 440                 445

Gly Leu Ile Tyr Ile Asp Tyr Asp Lys Asp Phe Asn Arg Gln Pro Lys
    450                 455                 460

Asp Ser Thr Lys Trp Phe Ser Lys Phe Leu Arg Thr
465                 470                 475
```

```
<210> SEQ ID NO 10
<211> LENGTH: 449
<212> TYPE: PRT
<213> ORGANISM: Bacillus circulans

<400> SEQUENCE: 10
```

| | | | | | | | | | | | | | | | |
|---|---|---|---|---|---|---|---|---|---|---|---|---|---|---|---|
| Ser | Ile | His | Met | Phe | Pro | Ser | Asp | Phe | Lys | Trp | Gly | Val | Ala | Thr | Ala |
| 1 | | | | 5 | | | | | 10 | | | | | 15 | |
| Ala | Tyr | Gln | Ile | Glu | Gly | Ala | Tyr | Asn | Glu | Asp | Gly | Arg | Gly | Met | Ser |
| | | | 20 | | | | | 25 | | | | | 30 | | |
| Ile | Trp | Asp | Thr | Phe | Ala | His | Thr | Pro | Gly | Lys | Val | Lys | Asn | Gly | Asp |
| | | | 35 | | | | | 40 | | | | | 45 | | |
| Asn | Gly | Asn | Val | Ala | Cys | Asp | Ser | Tyr | His | Arg | Val | Glu | Glu | Asp | Val |
| 50 | | | | | 55 | | | | | 60 | | | | | |
| Gln | Leu | Leu | Lys | Asp | Leu | Gly | Val | Lys | Val | Tyr | Arg | Phe | Ser | Ile | Ser |
| 65 | | | | | 70 | | | | | 75 | | | | | 80 |
| Trp | Pro | Arg | Val | Leu | Pro | Gln | Gly | Thr | Gly | Glu | Val | Asn | Arg | Ala | Gly |
| | | | | 85 | | | | | 90 | | | | | 95 | |
| Leu | Asp | Tyr | Tyr | His | Arg | Leu | Val | Asp | Glu | Leu | Leu | Ala | Asn | Gly | Ile |
| | | | 100 | | | | | 105 | | | | | 110 | | |
| Glu | Pro | Phe | Cys | Thr | Leu | Tyr | His | Trp | Asp | Leu | Pro | Gln | Ala | Leu | Gln |
| | | | 115 | | | | | 120 | | | | | 125 | | |
| Asp | Gln | Gly | Gly | Trp | Gly | Ser | Arg | Ile | Thr | Ile | Asp | Ala | Phe | Ala | Glu |
| | 130 | | | | | 135 | | | | | 140 | | | | |
| Tyr | Ala | Glu | Leu | Met | Phe | Lys | Glu | Leu | Gly | Gly | Lys | Ile | Lys | Gln | Trp |
| 145 | | | | | 150 | | | | | 155 | | | | | 160 |
| Ile | Thr | Phe | Asn | Glu | Pro | Trp | Cys | Met | Ala | Phe | Leu | Ser | Asn | Tyr | Leu |
| | | | | 165 | | | | | 170 | | | | | 175 | |
| Gly | Val | His | Ala | Pro | Gly | Asn | Lys | Asp | Leu | Gln | Leu | Ala | Ile | Asp | Val |
| | | | 180 | | | | | 185 | | | | | 190 | | |
| Ser | His | His | Leu | Leu | Val | Ala | His | Gly | Arg | Ala | Val | Thr | Leu | Phe | Arg |
| | | | 195 | | | | | 200 | | | | | 205 | | |
| Glu | Leu | Gly | Ile | Ser | Gly | Glu | Ile | Gly | Ile | Ala | Pro | Asn | Thr | Ser | Trp |
| | 210 | | | | | 215 | | | | | 220 | | | | |
| Ala | Val | Pro | Tyr | Arg | Arg | Thr | Lys | Glu | Asp | Met | Glu | Ala | Cys | Leu | Arg |
| 225 | | | | | 230 | | | | | 235 | | | | | 240 |
| Val | Asn | Gly | Trp | Ser | Gly | Asp | Trp | Tyr | Leu | Asp | Pro | Ile | Tyr | Phe | Gly |
| | | | | 245 | | | | | 250 | | | | | 255 | |
| Glu | Tyr | Pro | Lys | Phe | Met | Leu | Asp | Trp | Tyr | Glu | Asn | Leu | Gly | Tyr | Lys |
| | | | 260 | | | | | 265 | | | | | 270 | | |
| Pro | Pro | Ile | Val | Asp | Gly | Asp | Met | Glu | Leu | Ile | His | Gln | Pro | Ile | Asp |
| | | | 275 | | | | | 280 | | | | | 285 | | |
| Phe | Ile | Gly | Ile | Asn | Tyr | Tyr | Thr | Ser | Ser | Met | Asn | Arg | Tyr | Asn | Pro |
| | 290 | | | | | 295 | | | | | 300 | | | | |
| Gly | Glu | Ala | Gly | Gly | Met | Leu | Ser | Ser | Glu | Ala | Ile | Ser | Met | Gly | Ala |
| 305 | | | | | 310 | | | | | 315 | | | | | 320 |
| Pro | Lys | Thr | Asp | Ile | Gly | Trp | Glu | Ile | Tyr | Ala | Glu | Gly | Leu | Tyr | Asp |
| | | | | 325 | | | | | 330 | | | | | 335 | |
| Leu | Leu | Arg | Tyr | Thr | Ala | Asp | Lys | Tyr | Gly | Asn | Pro | Thr | Leu | Tyr | Ile |
| | | | 340 | | | | | 345 | | | | | 350 | | |
| Thr | Glu | Asn | Gly | Ala | Cys | Tyr | Asn | Asp | Gly | Leu | Ser | Leu | Asp | Gly | Arg |
| | | | 355 | | | | | 360 | | | | | 365 | | |
| Ile | His | Asp | Gln | Arg | Arg | Ile | Asp | Tyr | Leu | Ala | Met | His | Leu | Ile | Gln |
| | 370 | | | | | 375 | | | | | 380 | | | | |

```
Ala Ser Arg Ala Ile Glu Asp Gly Ile Asn Leu Lys Gly Tyr Met Glu
385                 390                 395                 400

Trp Ser Leu Met Asp Asn Phe Glu Trp Ala Glu Gly Tyr Gly Met Arg
            405                 410                 415

Phe Gly Leu Val His Val Asp Tyr Asp Thr Leu Val Arg Thr Pro Lys
            420                 425                 430

Asp Ser Phe Tyr Trp Tyr Lys Gly Val Ile Ser Arg Gly Trp Leu Asp
            435                 440                 445

Leu

<210> SEQ ID NO 11
<211> LENGTH: 446
<212> TYPE: PRT
<213> ORGANISM: Thermotoga maritima

<400> SEQUENCE: 11

Met Asn Val Lys Lys Phe Pro Glu Gly Phe Leu Trp Gly Val Ala Thr
  1               5                  10                  15

Ala Ser Tyr Gln Ile Glu Gly Ser Pro Leu Ala Asp Gly Ala Gly Met
             20                  25                  30

Ser Ile Trp His Thr Phe Ser His Thr Pro Gly Asn Val Lys Asn Gly
         35                  40                  45

Asp Thr Gly Asp Val Ala Cys Asp His Tyr Asn Arg Trp Lys Glu Asp
 50                  55                  60

Ile Glu Ile Ile Glu Lys Leu Gly Val Lys Ala Tyr Arg Phe Ser Ile
 65                  70                  75                  80

Ser Trp Pro Arg Ile Leu Pro Glu Gly Thr Gly Arg Val Asn Gln Lys
                 85                  90                  95

Gly Leu Asp Phe Tyr Asn Arg Ile Ile Asp Thr Leu Leu Glu Lys Gly
            100                 105                 110

Ile Thr Pro Phe Val Thr Ile Tyr His Trp Asp Leu Pro Phe Ala Leu
            115                 120                 125

Gln Leu Lys Gly Gly Trp Ala Asn Arg Glu Ile Ala Asp Trp Phe Ala
130                 135                 140

Glu Tyr Ser Arg Val Leu Phe Glu Asn Phe Gly Asp Arg Val Lys Asn
145                 150                 155                 160

Trp Ile Thr Leu Asn Glu Pro Trp Val Val Ala Ile Val Gly His Leu
                165                 170                 175

Tyr Gly Val His Ala Pro Gly Met Arg Asp Ile Tyr Val Ala Phe Arg
            180                 185                 190

Ala Val His Asn Leu Leu Arg Ala His Ala Arg Ala Val Lys Val Phe
            195                 200                 205

Arg Glu Thr Val Lys Asp Gly Lys Ile Gly Ile Val Phe Asn Asn Gly
210                 215                 220

Tyr Phe Glu Pro Ala Ser Glu Lys Glu Glu Asp Ile Arg Ala Val Arg
225                 230                 235                 240

Phe Met His Gln Phe Asn Asn Tyr Pro Leu Phe Leu Asn Pro Ile Tyr
                245                 250                 255

Arg Gly Asp Tyr Pro Glu Leu Val Leu Glu Phe Ala Arg Glu Tyr Leu
            260                 265                 270

Pro Glu Asn Tyr Lys Asp Asp Met Ser Glu Ile Gln Glu Lys Ile Asp
            275                 280                 285

Phe Val Gly Leu Asn Tyr Tyr Ser Gly His Leu Val Lys Phe Asp Pro
290                 295                 300
```

-continued

Asp Ala Pro Ala Lys Val Ser Phe Val Glu Arg Asp Leu Pro Lys Thr
305                 310                 315                 320

Ala Met Gly Trp Glu Ile Val Pro Gly Ile Tyr Trp Ile Leu Lys
            325                 330                 335

Lys Val Lys Glu Glu Tyr Asn Pro Pro Glu Val Tyr Ile Thr Glu Asn
            340                 345                 350

Gly Ala Ala Phe Asp Asp Val Ser Glu Asp Gly Arg Val His Asp
            355                 360                 365

Gln Asn Arg Ile Asp Tyr Leu Lys Ala His Ile Gly Gln Ala Trp Lys
    370                 375                 380

Ala Ile Gln Glu Gly Val Pro Leu Lys Gly Tyr Phe Val Trp Ser Leu
385                 390                 395                 400

Leu Asp Asn Phe Glu Trp Ala Glu Gly Tyr Ser Lys Arg Phe Gly Ile
                405                 410                 415

Val Tyr Val Asp Tyr Ser Thr Gln Lys Arg Ile Val Lys Asp Ser Gly
                420                 425                 430

Tyr Trp Tyr Ser Asn Val Val Lys Asn Asn Gly Leu Glu Asp
            435                 440                 445

<210> SEQ ID NO 12
<211> LENGTH: 448
<212> TYPE: PRT
<213> ORGANISM: Clostridium thermocellum

<400> SEQUENCE: 12

Met Ser Lys Ile Thr Phe Pro Lys Asp Phe Ile Trp Gly Ser Ala Thr
1               5                   10                  15

Ala Ala Tyr Gln Ile Glu Gly Ala Tyr Asn Glu Asp Gly Lys Gly Glu
            20                  25                  30

Ser Ile Trp Asp Arg Phe Ser His Thr Pro Gly Asn Ile Ala Asp Gly
        35                  40                  45

His Thr Gly Asp Val Ala Cys Asp His Tyr His Arg Tyr Glu Glu Asp
    50                  55                  60

Ile Lys Ile Met Lys Glu Ile Gly Ile Lys Ser Tyr Arg Phe Ser Ile
65                  70                  75                  80

Ser Trp Pro Arg Ile Phe Pro Glu Gly Thr Gly Lys Leu Asn Gln Lys
                85                  90                  95

Gly Leu Asp Phe Tyr Lys Arg Leu Thr Asn Leu Leu Leu Glu Asn Gly
            100                 105                 110

Ile Met Pro Ala Ile Thr Leu Tyr His Trp Asp Leu Pro Gln Lys Leu
        115                 120                 125

Gln Asp Lys Gly Gly Trp Lys Asn Arg Asp Ile Thr Asp Tyr Phe Thr
130                 135                 140

Glu Tyr Ser Glu Val Ile Phe Lys Asn Leu Gly Asp Ile Val Pro Ile
145                 150                 155                 160

Trp Phe Thr His Asn Glu Pro Gly Val Val Ser Leu Leu Gly His Phe
                165                 170                 175

Leu Gly Ile His Ala Pro Gly Ile Lys Asp Leu Arg Thr Ser Leu Glu
            180                 185                 190

Val Ser His Asn Leu Leu Leu Ser His Gly Lys Ala Val Lys Leu Phe
        195                 200                 205

Arg Glu Met Asn Ile Asp Ala Gln Ile Gly Ile Ala Leu Asn Leu Ser
    210                 215                 220

Tyr His Tyr Pro Ala Ser Glu Lys Ala Glu Asp Ile Glu Ala Ala Glu

```
                    225                 230                 235                 240

Leu Ser Phe Ser Leu Ala Gly Arg Trp Tyr Leu Asp Pro Val Leu Lys
                245                 250                 255

Gly Arg Tyr Pro Glu Asn Ala Leu Lys Leu Tyr Lys Lys Gly Ile
            260                 265                 270

Glu Leu Ser Phe Pro Glu Asp Leu Lys Leu Ile Ser Gln Pro Ile
        275                 280                 285

Asp Phe Ile Ala Phe Asn Asn Tyr Ser Ser Glu Phe Ile Lys Tyr Asp
    290                 295                 300

Pro Ser Ser Glu Ser Gly Phe Ser Pro Ala Asn Ser Ile Leu Glu Lys
305                 310                 315                 320

Phe Glu Lys Thr Asp Met Gly Trp Ile Ile Tyr Pro Glu Gly Leu Tyr
                325                 330                 335

Asp Leu Leu Met Leu Leu Asp Arg Asp Tyr Gly Lys Pro Asn Ile Val
                340                 345                 350

Ile Ser Glu Asn Gly Ala Ala Phe Lys Asp Glu Ile Gly Ser Asn Gly
            355                 360                 365

Lys Ile Glu Asp Thr Lys Arg Ile Gln Tyr Leu Lys Asp Tyr Leu Thr
        370                 375                 380

Gln Ala His Arg Ala Ile Gln Asp Gly Val Asn Leu Lys Ala Tyr Tyr
385                 390                 395                 400

Leu Trp Ser Leu Leu Asp Asn Phe Glu Trp Ala Tyr Gly Tyr Asn Lys
                405                 410                 415

Arg Phe Gly Ile Val His Val Asn Phe Asp Thr Leu Glu Arg Lys Ile
                420                 425                 430

Lys Asp Ser Gly Tyr Trp Tyr Lys Glu Val Ile Lys Asn Asn Gly Phe
            435                 440                 445

<210> SEQ ID NO 13
<211> LENGTH: 450
<212> TYPE: PRT
<213> ORGANISM: Thermoanaerobacter brockii

<400> SEQUENCE: 13

Met Ile Lys Leu Ala Lys Phe Pro Arg Asp Phe Val Trp Gly Thr Ala
1               5                   10                  15

Thr Ser Ser Tyr Gln Ile Glu Gly Ala Val Asn Glu Asp Gly Arg Thr
                20                  25                  30

Pro Ser Ile Trp Asp Thr Phe Ser Lys Thr Glu Gly Lys Thr Tyr Lys
            35                  40                  45

Gly His Thr Gly Asp Val Ala Cys Asp His Tyr His Arg Tyr Lys Glu
        50                  55                  60

Asp Val Glu Ile Leu Lys Glu Ile Gly Val Lys Ala Tyr Arg Phe Ser
65                  70                  75                  80

Ile Ala Trp Pro Arg Ile Phe Pro Glu Glu Gly Lys Tyr Asn Pro Lys
                85                  90                  95

Gly Met Asp Phe Tyr Lys Lys Leu Ile Asp Glu Leu Gln Lys Arg Asp
            100                 105                 110

Ile Val Pro Ala Ala Thr Ile Tyr His Trp Asp Leu Pro Gln Trp Ala
        115                 120                 125

Tyr Asp Lys Gly Gly Gly Trp Leu Asn Arg Glu Ser Ile Lys Trp Tyr
    130                 135                 140

Val Glu Tyr Ala Thr Lys Leu Phe Glu Glu Leu Gly Asp Ala Ile Pro
145                 150                 155                 160
```

```
Leu Trp Ile Thr His Asn Glu Pro Trp Cys Ser Ser Ile Leu Ser Tyr
            165                 170                 175

Gly Ile Gly Glu His Ala Pro Gly His Lys Asn Tyr Arg Glu Ala Leu
            180                 185                 190

Ile Ala Ala His His Ile Leu Leu Ser His Gly Glu Ala Val Lys Ala
            195                 200                 205

Phe Arg Glu Met Asn Ile Lys Gly Ser Lys Ile Gly Ile Thr Leu Asn
    210                 215                 220

Leu Thr Pro Ala Tyr Pro Ala Ser Glu Lys Glu Glu Asp Lys Leu Ala
225                 230                 235                 240

Ala Gln Tyr Ala Asp Gly Phe Ala Asn Arg Trp Phe Leu Asp Pro Ile
            245                 250                 255

Phe Lys Gly Asn Tyr Pro Glu Asp Met Met Glu Leu Tyr Ser Lys Ile
            260                 265                 270

Ile Gly Glu Phe Asp Phe Ile Lys Glu Gly Asp Leu Glu Thr Ile Ser
            275                 280                 285

Val Pro Ile Asp Phe Leu Gly Val Asn Tyr Tyr Thr Arg Ser Ile Val
    290                 295                 300

Lys Tyr Asp Glu Asp Ser Met Leu Lys Ala Glu Asn Val Pro Gly Pro
305                 310                 315                 320

Gly Lys Arg Thr Glu Met Gly Trp Glu Ile Ser Pro Glu Ser Leu Tyr
            325                 330                 335

Asp Leu Leu Lys Arg Leu Asp Arg Glu Tyr Thr Lys Leu Pro Met Tyr
            340                 345                 350

Ile Thr Glu Asn Gly Ala Ala Phe Lys Asp Glu Val Thr Glu Asp Gly
            355                 360                 365

Arg Val His Asp Asp Glu Arg Ile Glu Tyr Ile Lys Glu His Leu Lys
    370                 375                 380

Ala Ala Ala Lys Phe Ile Gly Glu Gly Gly Asn Leu Lys Gly Tyr Phe
385                 390                 395                 400

Val Trp Ser Leu Met Asp Asn Phe Glu Trp Ala His Gly Tyr Ser Lys
            405                 410                 415

Arg Phe Gly Ile Val Tyr Val Asp Tyr Thr Thr Gln Lys Arg Ile Leu
            420                 425                 430

Lys Asp Ser Ala Leu Trp Tyr Lys Glu Val Ile Leu Asp Asp Gly Ile
            435                 440                 445

Glu Asp
    450
```